(12) United States Patent
Alavi et al.

(10) Patent No.: US 9,925,296 B2
(45) Date of Patent: Mar. 27, 2018

(54) MESH ENCLOSED TISSUE CONSTRUCTS

(71) Applicant: The Regents of the University of California, Oakland, CA (US)

(72) Inventors: Seyedhamed Alavi, Irvine, CA (US); Arash Kheradvar, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/162,617

(22) Filed: Jan. 23, 2014

(65) Prior Publication Data

US 2014/0180399 A1 Jun. 26, 2014

Related U.S. Application Data

(63) Continuation-in-part of application No. 13/427,807, filed on Mar. 22, 2012, now Pat. No. 8,936,650.
(Continued)

(51) Int. Cl.
*A61L 27/04* (2006.01)
*C12N 5/071* (2010.01)
(Continued)

(52) U.S. Cl.
CPC .......... *A61L 27/047* (2013.01); *A61F 2/2415* (2013.01); *A61L 27/34* (2013.01);
(Continued)

(58) Field of Classification Search
CPC .... A61L 27/047; A61L 27/3808; A61L 27/56; A61L 27/3804; A61L 27/3826;
(Continued)

(56) References Cited

U.S. PATENT DOCUMENTS 4,191,218 A 3/1980 Clark et al.
6,103,255 A 8/2000 Levine et al.
(Continued)

FOREIGN PATENT DOCUMENTS

WO WO 00/42950 A2 7/2000

OTHER PUBLICATIONS

Ye et al., Enhancement of mesenchymal stem cell attachment to decellularized porcine aortic valve scaffold by in vitro coating with antibody against CD90: a preliminary study on antibody-modified tissue-engineered heart valve. Tissue Engineering: Part A, vol. 15, No. 1. (2009) pp. 1-11.*
(Continued)

*Primary Examiner* — Kara Johnson
(74) *Attorney, Agent, or Firm* — Knobbe, Martens, Olson & Bear, LLP

(57) ABSTRACT

Described is a heart valve leaflet manufactured from a mesh material. The mesh material may have an ability to capture circulatory/stationary/migratory cells of the body to become biologically active. In some cases, the mesh material is coated with a bioactive material, such as a molecule that binds to a cell adhesion molecule (CAM), a growth factor, an extracellular matrix molecule, a subendothelial extracellular matrix molecule or a peptide. The mesh has a stiffness that is comparable to a native heart valve leaflet, such that it functionally mimics a native heart valve.

18 Claims, 15 Drawing Sheets

Related U.S. Application Data

(60) Provisional application No. 61/756,451, filed on Jan. 24, 2013, provisional application No. 61/559,694, filed on Jan. 19, 2012, provisional application No. 61/540,330, filed on Sep. 28, 2011, provisional application No. 61/496,369, filed on Jun. 13, 2011, provisional application No. 61/466,882, filed on Mar. 23, 2011.

(51) Int. Cl.

| | |
|---|---|
| *A61L 27/34* | (2006.01) |
| *A61L 27/38* | (2006.01) |
| *A61L 27/54* | (2006.01) |
| *A61L 27/56* | (2006.01) |
| *A61F 2/24* | (2006.01) |
| *C12N 5/00* | (2006.01) |

(52) U.S. Cl.
CPC ....... *A61L 27/3804* (2013.01); *A61L 27/3808* (2013.01); *A61L 27/3826* (2013.01); *A61L 27/54* (2013.01); *A61L 27/56* (2013.01); *C12N 5/0068* (2013.01); *C12N 5/0691* (2013.01); *A61L 2300/414* (2013.01); *A61L 2300/606* (2013.01); *A61L 2400/18* (2013.01); *A61L 2430/20* (2013.01); *C12N 2501/15* (2013.01); *C12N 2513/00* (2013.01); *C12N 2533/10* (2013.01); *C12N 2533/54* (2013.01); *C12N 2535/00* (2013.01)

(58) Field of Classification Search
CPC .... A61L 27/54; A61L 27/34; A61L 2300/606; A61L 2430/20; A61L 2300/414; A61L 2400/18; C12N 5/0068; C12N 5/0691; C12N 2513/00; C12N 2535/00; C12N 2501/15; C12N 2533/54; A61F 2/2415
USPC .............................. 623/2.13, 2.12
See application file for complete search history.

(56) References Cited

U.S. PATENT DOCUMENTS

| | | | |
|---|---|---|---|
| 6,139,575 | A | 10/2000 | Shu et al. |
| 6,337,198 | B1 | 1/2002 | Levene et al. |
| 6,461,382 | B1 | 10/2002 | Cao |
| 7,422,603 | B2 | 9/2008 | Lane |
| 7,575,759 | B2 | 8/2009 | Murphy et al. |
| 7,635,592 | B2 | 12/2009 | West et al. |
| 7,846,728 | B2 | 12/2010 | Brooks et al. |
| 7,871,435 | B2 | 1/2011 | Carpentier et al. |
| 7,914,808 | B2 | 3/2011 | Malaviya et al. |
| 7,968,026 | B1 | 6/2011 | Teoh et al. |
| 7,972,377 | B2 | 7/2011 | Lane |
| 8,017,396 | B2 | 9/2011 | Kumar et al. |
| 8,039,258 | B2 | 10/2011 | Harris et al. |
| 8,071,007 | B1 | 12/2011 | Teoh et al. |
| 8,137,686 | B2 | 3/2012 | Kladakis et al. |
| 2003/0027332 | A1 | 2/2003 | LaFrance et al. |
| 2005/0002982 | A1 | 1/2005 | Mooney et al. |
| 2005/0143810 | A1 | 6/2005 | Dauner et al. |
| 2005/0181016 | A1 | 8/2005 | Freyman et al. |
| 2006/0246584 | A1 | 11/2006 | Covelli |
| 2006/0253192 | A1 | 11/2006 | Atala et al. |
| 2007/0041952 | A1 | 2/2007 | Guilak et al. |
| 2009/0163612 | A1 | 6/2009 | Brady et al. |
| 2009/0252795 | A1 | 10/2009 | Smyth |
| 2010/0249922 | A1 | 9/2010 | Li et al. |
| 2012/0015331 | A1 | 1/2012 | Wood et al. |

OTHER PUBLICATIONS

Wise et al., Extracellular matrix molecules facilitating vascular biointegration. Journal of Functional Biomaterials, vol. 3, No. 3 (2012) pp. 569-587.*
He et al., Fabrication of collagen-coated biodegradable polymer nanofiber mesh and its potential for endothelial cells growth. Biomaterials, vol. 26, No. 36 (Dec. 2005) pp. 7606-7615.*
Abu-Omar, Y. et al. 2008 "Prosthetic heart valves" *Surgery* 26: 496-500.
Aikawa, E. et al. 2006 "Human semilunar cardiac valve remodeling by activated cells from fetus to adult: Implications for postnatal adaptation, pathology and tissue engineering" *Circulation* 113: 1344-1352.
Alavi, S.H. et al. 2011 "A hybrid self-regenerative tissue approach as a proper alternative for prosthetic heart valves" *ASAIO J* 57: 88.
Alavi, S.H. et al. 2012 "Metal mesh scaffold for tissue engineering of membranes" *Tissue Eng Part C* 18: 293-301.
Adamczyk, M.M. et al. 2002 "Biaxial strain distributions in explanted porcine bioprosthetic valves" *J Heart Valve Dis* 11: 686-695.
Appleton, A.J.E. et al. 2009 "Vascular smooth muscle cells as a valvular interstitial cell surrogate in heart valve tissue engineering" *Tissue Engineering Part A* 15: 3889-3897.
Apte, S.S. et al. 2011 "Current developments in the tissue engineering of autologous heart valves: Moving towards clinical use" *Future Cardiology* 7: 77-97.
Bobak, D. et al. 1986 "Characterization of c1q receptor expression on human phagocytic cells: Effects of pdbu and fmip" *J Immunol* 136: 4604-4610.
Boontheekul, T. et al. 2003 "Protein-based signaling systems in tissue engineering" *Current Opinion in Biotechnology* 14: 559-565.
Boyan, B.D. et al. 1996 "Role of material surfaces in regulating bone and cartilage cell responses" *Biomaterials* 17: 137.
Breuer, C.K. et al. 2004"Application of tissue-engineering principles toward the development of semilunar heart valve substitute" *Tissue Engineering* 10: 1725-1736.
Butcher, J.T. et al. 2006 "Profiles of valvular and vascular endothelial cells reveal phenotypic differences: influence of shear stress" *Arterioscler Throm Vasc Biol* 26: 69-77.
Chen, J. et al. 2009 "Spectroscopic characterization and microscopic imaging of extracted and in situ cutaneous collagen and elastic tissue components under two-photon excitation" *Skin Res Technol* 15: 416-426.
Cox, G. et al. 2003 "3-Dimensional imaging of collagen using second harmonic generation" *J Struct Biol* 141: 53-62.
D'Arcy, J.L. et al. 2011 "Valvular heart disease: The next cardiac epidemic" *Heart* 97: 91-93.
Deymier-Black, A.C. et al. 2010 "Synchrotron x-ray diffraction study of load partitioning during elastic deformation of bovine dentin" *Acta Biomater* 6: 2172-2180.
Ferrans, V.J. et al. 1978 "Structural changes in glutaraldehyde-treated porcine heterografts used as substitute cardiac valves: Transmission and scanning electron microscopic observations in 12 patients" *Am J Cardiol* 41: 1159-1184.
Flanagan, T.C. et al. 2003 "Living artificial heart valve alternatives: A review" *Eur Cell Mater* 6: 28-45.
Gan, B.K. et al. 2007 "Comparison of protein surface attachment on untreated and plasma immersion ion implantation treated polystyrene: protein islands and carpet" *Langmuir* 23: 2741-2746.
Georgiou, E. et al. 2000 "Second and third optical harmonic generation in type I collagen by nanosecond laser irradiation, over a broad spectral region" *Optics Communications* 176: 253-260.
Grande-Allen, K. et al. 2011 "The heterogeneous biomechanics and mechanobiology of the mitral valve: implications for tissue engineering" *Current Cardiology Reports* 13: 113-120.
Hahn, M.S. et al. 2007 "Physiologic pulsatile flow bioreactor conditioning of poly(ethylene glycol) based tissue engineered vascular grafts" *Annals of Biomedical Engineering* 35: 190-200.
Hara, M. et al. 2006 "Imaging pancreatic betacells in the intact pancreas" *Am J Physiol Endocrinol Metab* 290: E1041-1047.
Hildebrant, J. et al. 1969 "Stress-strain relations of tissue sheets undergoing uniform two-dimensional stretch" *J Appl Physiol* 27: 758-762.

(56) References Cited

OTHER PUBLICATIONS

Hoerstrup, S.P. et al. 2000 "Functional living trileaflet heart valves grown in vitro" *Circulation* 102: 111-44-49.
Hoffmann, G. et al. 2008 "Durability of bioprosthetic cardiac valves" *Dtsch Arztebl Int* 105: 143-148.
Hori, J. et al. 2003 "Neural progenitor cells lack immunogenicity and resist destruction as allografts" *Stem Cells* 21: 405-416.
Iijima, K. et al. 2004 "Dissecting the pathological effects of human abeta40 and abeta42 in *Drosophila*: A potential model or Alzheimer's Disease" *Proc Natl Acad Sci USA* 101: 6623-6628.
Jansen, L.P. et al. 2004 "Surgical mesh as a scaffold for tissue regeneration in the esophagus" *European Surgical Research* 36: 104-111.
Khaled, A. et al. 2002 "Cytokines and the control of lymphoid homeostasis" *Nat Rev Immunol* 2: 817-830.
Kheradvar, A. et al. 2004 "Evaluation of isovolumic relaxation phase in the process of ventricular remodeling following myocardial infarction" *Engineering in Medicine and Biology Society (IEMBS) 26th Annual International conference of the IEEE* 2: 3654-3657.
Kheradvar, A. et al. 2006 "Estimation of elastic and viscous properties of the left ventricle based on annulus plane harmonic behavior" *Conference Proceedings, Annual International Conference of the IEEE Engineering in Medicine and Biology Society,* p. 4.
Kheradvar, A. et al. 2006 "An in vitro study of changing profile heights in mitral bioprostheses and their influence on flow" *ASAIO J* 52: 34-38.
Kheradvar, A. et al. 2006 "Assessment of left ventricular viscoelastic components based on ventricular harmonic behavior" *Cardiovascular Engineering* 6: 30-39.
Kheradvar, A. et al. 2009 "On mitral valve dynamics and its connection to early diastolic flow" *Annals of Biomedical Engineering* 37: 1-13.
Kheradvar, A. et al. 2011 "A hybrid self-renewal engineered tissue for heart valve leaflets" *Society of Heart Valve Disease, 6th Biennial Meeting.*
Kheradvar, A. et al. 2012 "The effects of dynamic saddle annulus and leaflet length on transmitral flow pattern and leaflet stress of a bioprosthetic mitral Valve" *J Heart Valve Dis* 21(2): 225-233.
Kieswener, K. et al. 1996 "Surface roughness modulates the local production of growth factors and cytokines by osteoblast-like mg-63 cells" *J Biomed Mater Res* 32: 55.
Kondyurin, A. et al. 2008 "Calcium phosphate formation on plasma immersion ion implanted low density polyethylene and polytetrafluoroethylene surfaces" *J Materials Science: Materials in Medicine* 19: 1145-1153.
Ku, C.H. et al. 2006 "Collagen synthesis by mesenchymal stem cells and aortic valve interstitial cells in response to mechanical stretch" *Cardiovasc Res* 71: 548-556.
Kuznetsova, N. et al. 1998 "Sugars and polyols inhibit fibrillogenesis of type I collagen by disrupting hydrogen-bonded water bridges between the helices" *Biochemistry* 37: 11888-11895.
Leitao, E. et al. 1998 "In vitro testing of surface-modified biomaterials" *J Materials Science: Materials in Medicine* 9: 543-548.
Liu, Y.C. et al. 2003 "High-resolution confocal imaging and three-dimensional rendering" *Methods* 30: 86-93.
Liu et al. 2004 "Surface modification of titanium, titanium alloys and related materials for biomedical applications" *Materials Science and Engineering R* 47: 49-121.
Liu, A.C. et al. 2007 "The emerging role of valve interstitial cell phenotypes in regulating heart valve pathobiology" *Am J Pathol* 171: 1407-1418.
Liu, W.F. et al. 2011 "Real-time in vivo detection of biomaterial-induced reactive oxygen species" *Biomaterials* 32: 1796-1801.
Long, J. et al. 2003 "Elastic fiber production in cardiovascular tissue-equivalents" *Matrix Biology* 22: 339-350.
Ma, M. et al. 2011 "Development of cationic polymer coatings to regulate foreign-body responses" *Advanced Materials* 23: H189-H194.

Maitz, M.F. et al. 2002 "Ion beam treatment of titanium surfaces for enhancing deposition of hydroxyapatite from solution" *Biomolecular Engineering* 19: 269-272.
McGuigan, A.P. et al. 2008 "The thrombogenicity of human umbilical vein endothelial cell seeded collagen modules" *Biomaterials* 29: 2453-2463.
Mendelson, K. et al. 2006 "Heart valve tissue engineering: Concepts, approaches, progress and challenges" *Annals of Biomed Engineering* 34: 1799-1619.
Misfeld et al. 2007 "Heart valve macro- and microstructure" *Phil Trans R Soc B* 362: 1421-1436.
Mulholland, D.L. et al. 1996 "Cell biology of valvular interstitial cells" *Can J Cardiol* 12: 231-236.
Na, G.C. et al. 1986 "In vitro collagen fibril assembly in glycerol solution: evidence for a helical cooperative mechanism involving microfibrils" *Biochemistry* 25: 958-966.
Nkomo, V.T. et al. 2006 "Burden of valvular heart diseases: A population-based study" *Lancet* 368: 1005-1011.
Oshida, Y. et al. 1993 "Effects of shot-peening on surface contact angles of biomaterials" *J Materials Science: Materials in Medicine* 4: 443-447.
Pignataro, B. et al. 1997 "Improved cell adhesion to ion beam-irradiated polymer surfaces" *Biomaterials* 18: 1461-1470.
Pypen, C.M.J.M. 1997 "Characterization of microblasted and reactive ion etched surfaces on the commercially pure metals niobium, tantalum, and titanium" *J Materials Science: Materials in Medicine* 6: 781-784.
Rabkin-Aikawa, E. et al. 2004 "Dynamic and reversible changes of interstitial cell phenotype during remodeling of cardiac valves" *J Heart Valve Dis* 13: 841-847.
Rabkin-Aikawa, E. et al. 2005 "Cardiovascular tissue engineering" *Cardiovascular Pathology* 11: 305-317.
Rabkin-Aikawa, E. et al. 2005 "Heart valve regeneration" *Adv Biochem Eng Biotechnol* 94: 141-179.
Sacks, M.S. et al. 2009 "Bioengineering challenges for heart valve tissue engineering" *Annual Rev of Biomed Engineering* 11: 289-313.
Saidi, I.S. et al. 1995 "Mie and rayleigh modeling of visible-light scattering in neonatal skin" *Appl Opt* 34: 7410-7418.
Salvador-Morales, C. et al. 2009 "Immunocompatibility properties of lipid-polymer hybrid nanoparticles with heterogeneous surface functional groups" *Biomaterials* 30: 2231-2240.
Schenke-Layland, K. et al. 2006 Impact of cryopreservation on extracellular matrix structures of heart valve leaflets *Ann Thorac Surg* 81: 918-926.
Schenke-Layland, K. et al. 2008 Non-invasive multiphoton imaging of extracellular matrix structures: *J Biophotonics* 1: 451-462.
Shah, S.R. V.N. 2008 "The effect of glycosaminoglycan stabilization on tissue buckling in bioprosthetic heart valves" *Biomaterials* 29: 1645-1653.
Shenton, M.J. et al. 2005 "Ultralow energy ion beam surface modification of low density polyethylene" *J Physical Chem B* 109: 22185-22088.
Shinoka, T. et al. 1995 "Tissue engineering heart valves: Valve leaflet replacement study in a lamb model" *Ann Tnorac Surg* 60: S513-516.
Shinoka, T. et al. 1996 "Tissue-engineered heart valves: Autologous valve leaflet replacement study in a lamb model" *Circulation* 94: 164-168.
Smith, D.B. et al. 1999 "Fatigue-induced changes in bioprosthetic heart valve three dimensional geometry and the relation to tissue damage" *J Heart Valve Dis* 8: 25-33.
Steinhoff, G. et al. 2000 "Tissue engineering of pulmonary heart valves on allogenic acellular matrix conduits: in vivo restoration of valve tissue" Circulation 102:III-50-55.
Stephens, E.H. et al. 2010 "Age-related changes in material behavior of porcine mitral and aortic valves and correlation to matrix composition" *Tissue Engineering Part A* 16: 867-878.
Sugita, Y. et al. 2009 "Experimental evaluation of a new antithrombogenic stent using ion beam surface modification" *Artificial Organs* 33: 456-463.
Syedain, Z.H. et al. 2009 "Controlled cyclic stretch bioreactor for tissue-engineered heart valves" *Biomaterials* 30: 4078-4084.

(56) References Cited

OTHER PUBLICATIONS

Tedder, M.E. et al. 2010 "Assembly and testing of stem cells-seeded layered collagen constructs for heart valve tissue engineering" *Tissue Eng Part A* 17: 25-36.

Thubrikar, M. et al. 1983 "Role of mechanical stress in calcification of aortic bioprosthetic valves" *J Thorac Cardiovasc Surg* 86: 115-125.

Van Den Broek, C.N. et al. 2008 "Medium with blood-analog mechanical properties for cardiovascular tissue culturing" *Biorheology* 45: 651-661.

Van Geemen, D. et al. 2011 "Decreased mechanical properties of heart valve tissue properties of heart valve tissue constructs cultured in platelet lysate as compared to fetal bovine serum" *Tissue Engineering Part C Methods* 17: 607-617.

Vesely, I. et al. 1988 "Tissue buckling as a mechanism of bioprosthetic valve failure" *Ann Thorac Surg* 46: 302-308.

Vesely, I. et al. 2001 "Tissue damage and calcification may be independent mechanisms of bioprosthetic heart valve failure" *J Heart Valve Dis* 10: 471-477.

Vesely, I. 2005 "Heart valve tissue engineering" *Circ Res* 97: 743-755.

Walachova, K. et al. 2002 "Colonization of ion-modified polyethylene with vascular smooth muscle cells in vitro" *Biomaterials* 23: 2989-2996.

Wells, P.B. et al. 2006 "Influence of glycerol on the mechanical reversibility and thermal damage susceptibility of collagenous tissues" *IEEE Trans Biomed Eng* 53: 747-753.

Wirrig, E.E. et al. 2011 "Differential expression of cartilage and bone-related proteins in pediatric and adult diseased aortic valves" *J Molec and Cell Cardiology* 50: 561-569.

Yeh, A.T. et al. 2003 "Reversible dissociation of collagen in tissues" *J Invest Dermatol* 121: 1332-1335.

Zioupos, P. et al. 1992 "Mechanical and optical anisotrpy of bovine pericardium" *Med Biol Eng Comput* 30: 76-82.

Trepanier, C. et al. 2000 "Corrosion Resistance and Biocompatibility of Passivated Nitinol" in *Shape Memory Implants* (ed.) L'H. Yahia, ndc, pp. 35-45.

Alavi, S.H. et al. 2011 "A hybrid self-regenerative tissue approach as a proper alternative for prosthetic heart valves" *ASAIO J* 57: p. 88.

Alavi, H. et al. 2011 "A hybrid self-renewal engineered tissue for heart valve leaflets" Society of Heart Valve Disease, 6th Biennial Meeting (Abstract).

Fong, P. et al. 2006 "The use of polymer based scaffolds in tissue-engineered heart valves" Progress in Pediatric Cardiology 21: 193-199.

Mulholland D.L. and Gotlieb, A.I. 1996 "Cell biology of valvular interstitial cells" Can J Cardiol 12: 231-236.

Van Den Broek, C.N. et al. 2008 "Medium with blood-analog mechanical properties for cardiovascular tissue culturing" Bioreheology 45: 651-661.

Zund, G. et al. 1998 "Tissue engineering: A new approach in cardiovascular surgery; Seeding of human fibroblasts followed by human endothelial cells on resorbable mesh" *European Journal of Cardio-thoracic Surgery* 13: 160-164.

* cited by examiner

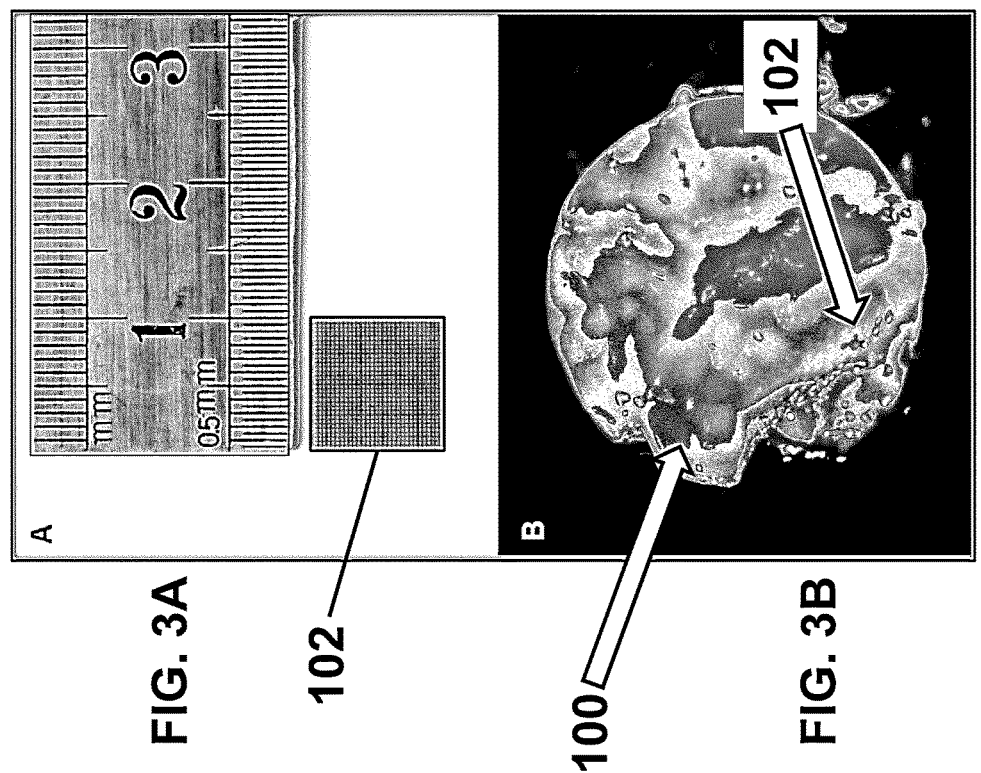

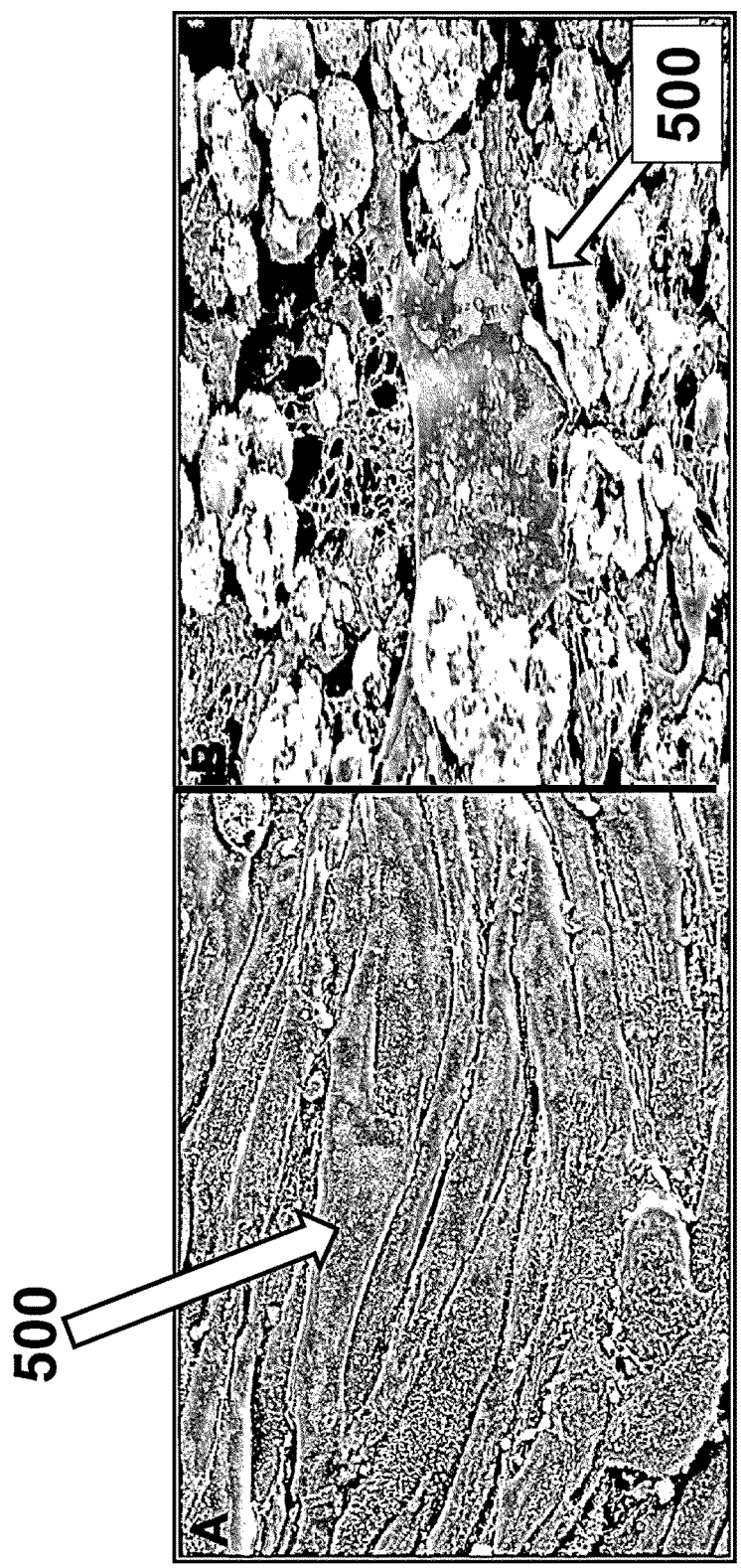

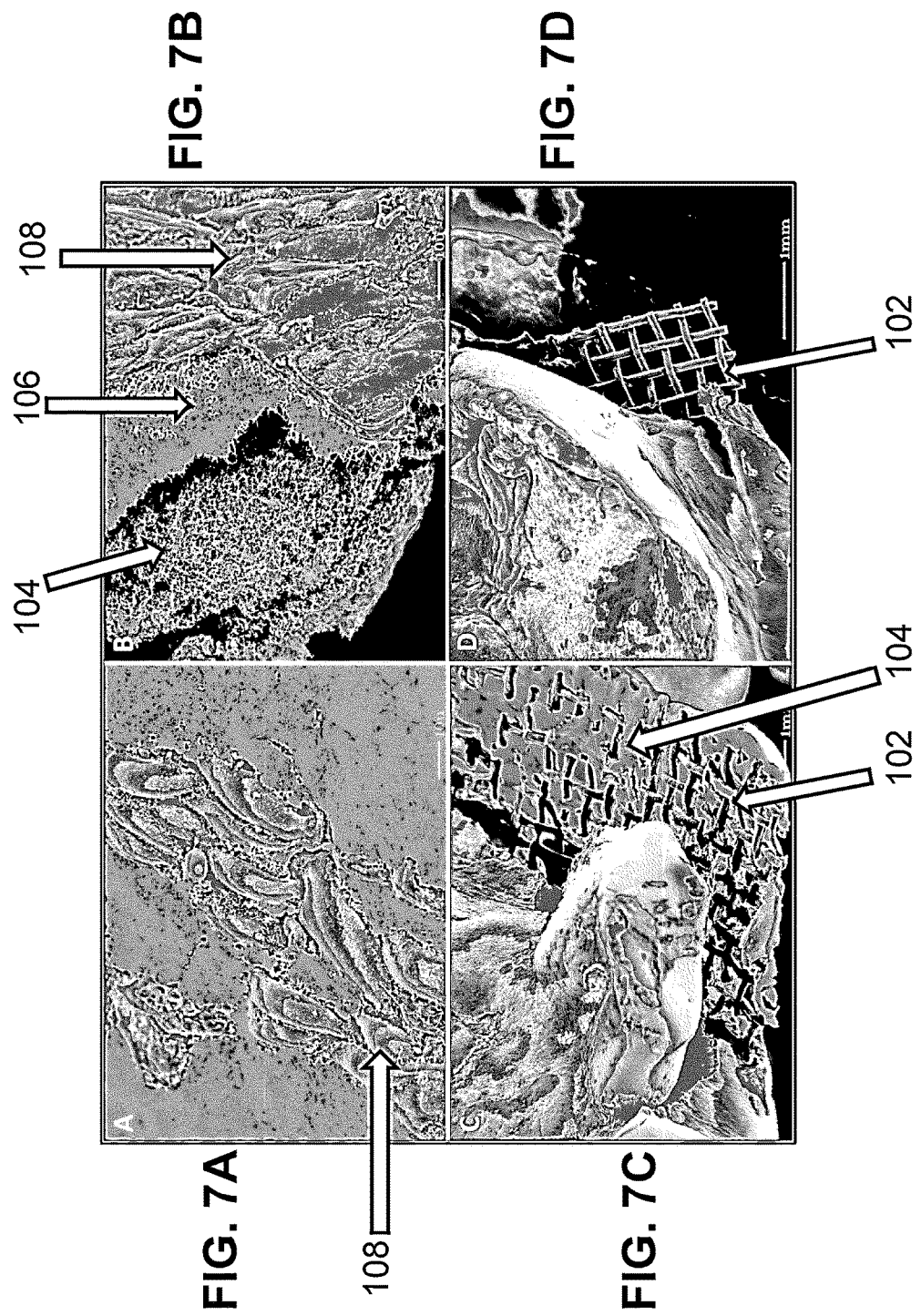

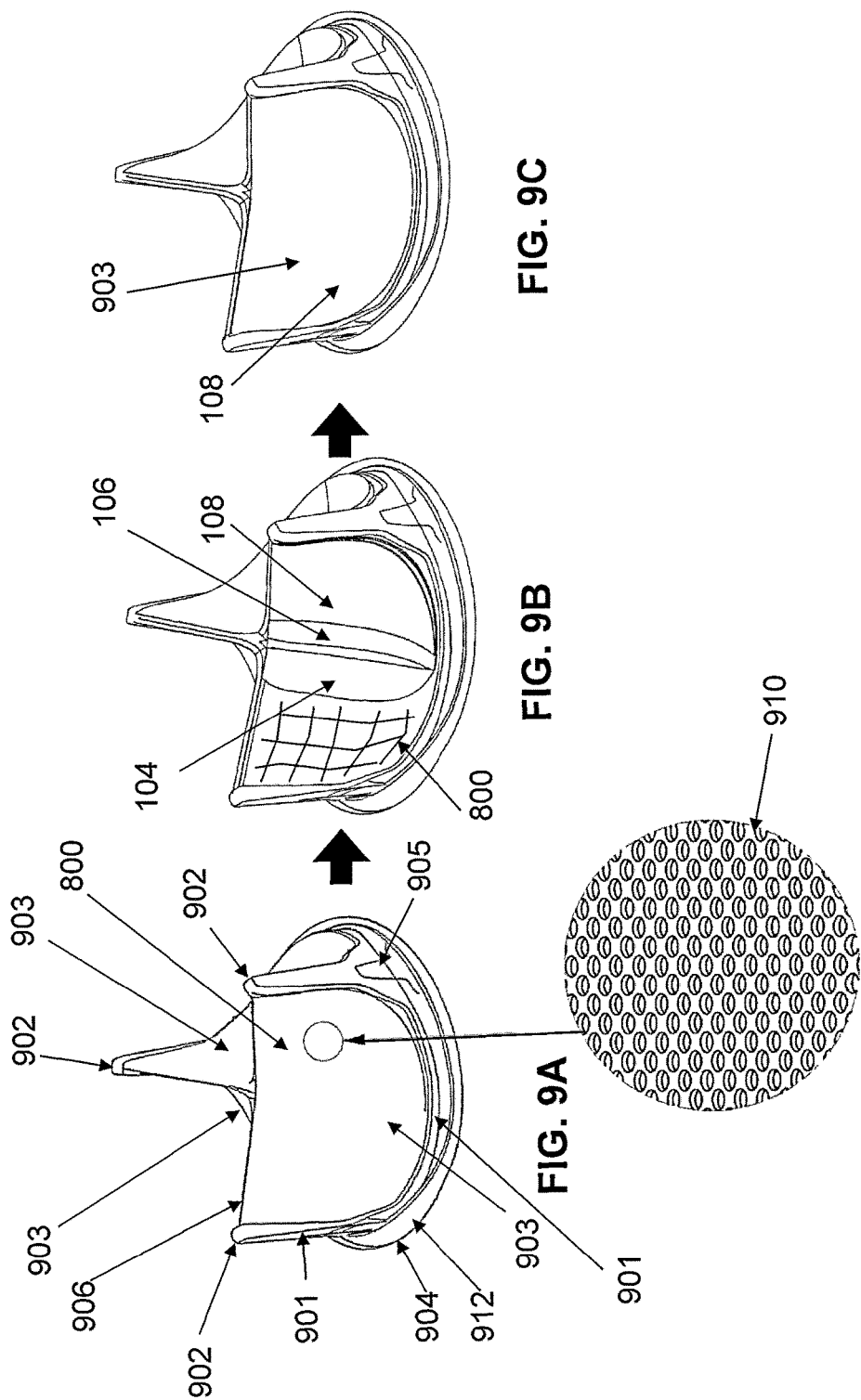

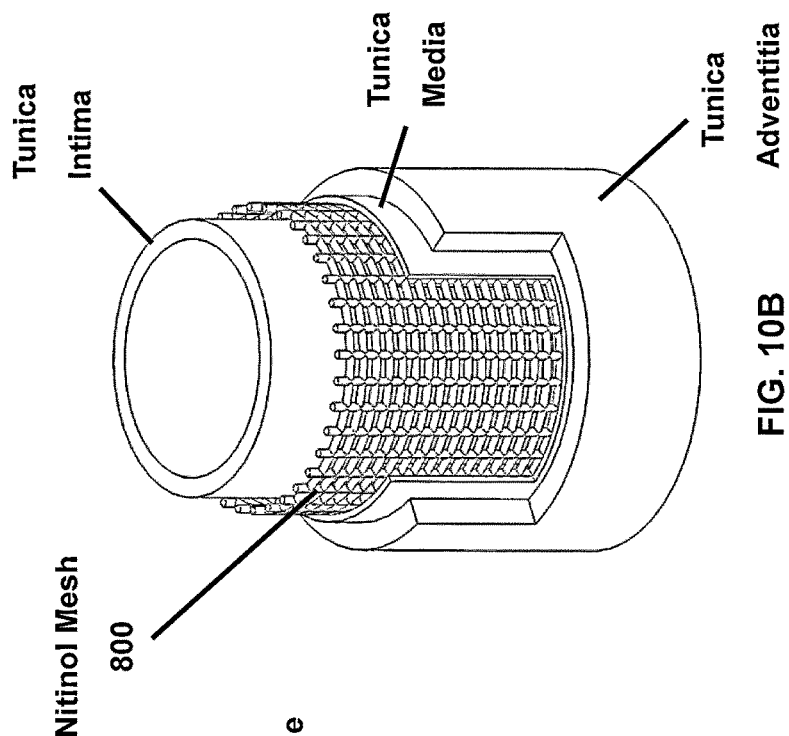
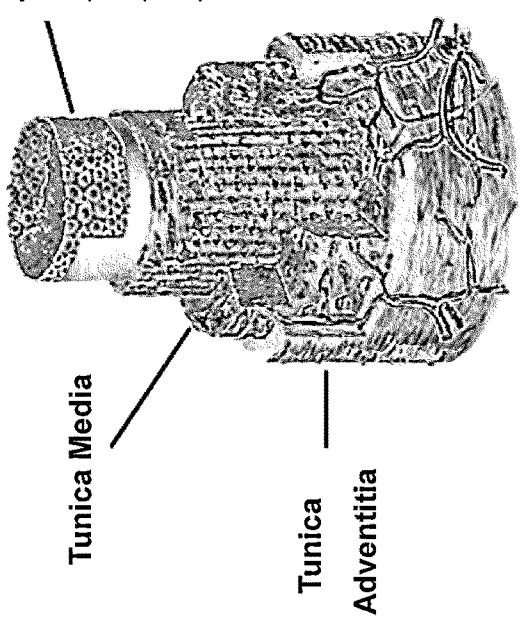
FIG. 10A
FIG. 10B

MESH ENCLOSED TISSUE CONSTRUCTS

FIELD OF THE INVENTION

The invention pertains to a heart valve leaflet manufactured from a mesh material. The mesh material may have an ability to capture circulatory/stationary/migratory cells of the body to become biologically active.

BACKGROUND OF THE INVENTION

Engineering of the membrane-like tissue structures with ability to remodel and regenerate is currently an unresolved subject in the field of tissue engineering. Several attempts with minimal success have been made to create functional viable membrane tissues such as heart valve leaflet with the ability to grow, repair, and remodel. Shinoka et al. fabricated single leaflet heart valves by sequentially seeding ovine fibroblasts and endothelial cells on a bioabsorbable polymer composed of a polyglactin woven mesh surrounded by two nonwoven polyglycolic acid mesh sheets. (See Shinoka, T., Breuer, C. K., Tanel, R. E., Zund, G., Miura, T., Ma, P. X., Langer, R., Vacanti, J. P., and Mayer J. E. Tissue engineering heart valves: Valve leaflet replacement study in a lamb model. Ann Thorac Surg, 60, 13, 1995). Hoerstrup et al. fabricated a trileaflet heart valve using nonwoven polyglycolic acid mesh, a bioabsorbable polymer, sequentially seeded with ovine myofibroblasts and endothelial cells made using a pulse duplicator in vitro system. (See Hoerstrup, S. P., Sodian, R., Daebritz, S., Wang, J., Bacha, E. A., Martin, D. P., Moran, A. M., Guleserian, K. J., Sperling, J. S., Kaushal, S., Vacanti, J. P., Schoen, F. J., and Mayer, J. E. Jr. Functional living trileaflet heart valves grown in vitro. Circulation, 102, 44, 2000). Sodian et al. constructed trileaflet heart valve scaffolds fabricated from seeding ovine arterial vascular cells on a polyhydroxyoctanoate material. (See Sodian, R., Hoerstrup, S. P., Sperling, J. S., Daebritz, S., Martin, D. P., Moran, A. M., Kim, B. S., Schoen, F. J., Vacanti, J. P., and Mayer, J. E. Jr. Early in vivo experience with tissue-engineered trileaflet heart valves. Circulation, 102, suppl III, 2000). Sutherland et al. created autologous semilunar heart valves in vitro using mesenchymal stems cells and a biodegradable scaffold made of polyglycolic acid and poly-L-lactic acid. (See Sutherland, F. W., Perry, T. E., Yu, Y., Sherwood, M. C., Rabkin, E., Masuda, Y., Garcia, A., McLellan, D. L., Engelmayr, G. C., Sacks, M. S., Schoen, F. J., and Mayer J. E. Jr. From stem cells to viable autologous semilunar heart valve. Circulation, 111, 2783, 2005). Drawbacks to the approaches described above include structural vulnerability, short term functionality, and limited mechanical properties of the membrane constructs.

Scaffolds are critical components of the engineered tissues that allow them to be formed in vitro and remain secure in vivo when implanted in a host. Several approaches have been taken to develop scaffolds for tissue membranes. The most widely used method involves biodegradable naturally-derived or synthetic polymers, where the polymer eventually degrades by normal metabolic activity, while the biological matrix is formed. To have viable tissue, the rate of scaffold degradation should be proportional to the rate of tissue formation to guarantee mechanical stability over time. The poor control of enzymatic degradation and low mechanical performance are two major limitations of naturally derived polymers. In contrast, synthetic polymers can be prepared precisely with respect to structure and function. However, most of them produce toxic chemicals when they degrade in vivo, and due to lack of receptor-binding ligands, they may not provide a good environment for adhesion and proliferation of cells.

Another option for creating scaffolds is to use decellularized xenogenic tissues, which has some advantages over polymeric materials. Decellularized tissues provide a unique scaffold, which is essentially composed of extracellular matrix (ECM) proteins that serve as an intrinsic template for cells. However, the process of decellularization cannot completely remove the trace of cells and their debris. These remnants not only increase the potential of an immunogenic reaction, but also result in increased tissue susceptibility to calcification.

Another, albeit less developed, strategy involves creating a scaffold with completely biological matrix components. This approach has advantages over using polymeric materials or decellularized xenogenic tissues. For example, large amounts can be produced from xenogenic sources, which can readily accommodate cellular ingrowth without cytotoxic degradation products. However, this strategy is restricted due to mechanical fragility of the scaffold and the low potentials for creating complex tissue structures.

Thus, a continuing need exists for a tissue construct that is strong enough to resist forces that exist inside a body, while possessing biocompatible surfaces.

SUMMARY OF THE INVENTION

Some embodiment relate to a heart valve leaflet comprising a mesh material.

In some embodiments, the mesh material is made of a metal.

In some embodiments, the metal is nitinol.

In some embodiments, the leaflet has an ability to capture circulatory/stationary/migratory cells of the body to become biologically active.

In some embodiments, the leaflet has a modified surface, which facilitates growth of a tissue layer on the leaflet, such that the mesh may become enclosed in the tissue layer.

In some embodiments, a bioactive material is used to coat the leaflet to optimize cell capture and/or to actively recruit cells and/or provide cell differentiation guidance.

In some embodiments, the bioactive material is selected from the group consisting of a molecule that binds to a cell adhesion molecule (CAM), a growth factor, an extracellular matrix molecule, a subendothelial extracellular matrix molecule and a peptide.

In some embodiments, the molecule that binds to a CAM is a CD34 antibody.

In some embodiments, the growth factor is selected from the group consisting of epidermal growth factor (EGF), fibroblast growth factor 1 (FGF1), FGF2, FGF3, FGF4, vascular endothelial growth factor-A (VEGF-A), VEGF-B, VEGF-C, VEGF-D, and placental growth factor (PGF).

In some embodiments, the subendothelial extracellular matrix molecule is selected from the group consisting of fibulin-5 and fibrillin-1.

In some embodiments, the peptide is an RGD-peptide.

In some embodiments, the surface of the leaflet is modified by plasma coating.

In some embodiments, the surface of the mesh is micropatterned to enhance cell binding.

In some embodiments, the mesh has stiffness that is comparable to a native heart valve leaflet, wherein it mimics native heart valve function.

In some embodiments, the mesh has a hole diameter of between 0.0005-0.0200 inches.

In some embodiments, the mesh has a thickness of between 0.0004-0.0100 inches.

Some embodiments relate to a heart valve comprising a heart valve leaflet as disclosed herein.

Some embodiments are directed to a scaffold that is strong enough to resist forces that exist inside a body, while possessing biocompatible surfaces. The scaffold is formed of a layer of mesh (e.g., Stainless Steel or Nitinol) that is tightly enclosed by a multi-layer biological matrix. The biological matrix can include any desired number of layers, such as a first layer (smooth muscle cells) formed directly on the metal mesh, a second layer (fibroblast/myofibroblast cells) formed on the first layer, and a third layer (endothelial cells) formed on the second layer.

The scaffold can be formed to operate as a variety of tissues, such as a heart valve or vascular graft. For example, the mesh and corresponding biological matrix can be formed as leaflets, such that the scaffold is operable as a tissue heart valve. In this aspect, the scaffold includes a flexible frame having a saddle-shaped base with at least two upstanding posts, with the leaflets each having a peripheral free portion extending between the posts and a fixed portion attached with the base.

In another aspect, the scaffold is formed as a vascular graft. In this aspect, the layer of mesh is a tubular wire mesh, with the biological matrix formed around the mesh to completely conceal the mesh therein.

As can be appreciated by one skilled in the art, the present invention is also directed to the method of forming the scaffold described herein. The method includes a plurality of acts, such as preparing a layer of mesh and growing a biological matrix around the layer of mesh such that the biological matrix tightly encloses the layer of mesh.

In another aspect, the act of preparing the layer of mesh further comprises a preparation technique, or any combination thereof, selected from a group consisting of polishing the layer of mesh; acid washing the layer of mesh; ultrasonic clean washing the layer of mesh; and glow discharging the layer of mesh.

Additionally, the act of preparing the layer of mesh further comprises an act of ion beam surface modification to provide a smooth surface and ensure the biocompatibility and enhanced cell attachment.

In yet another aspect, growing a biological matrix around the layer of mesh further comprises an act of providing collagen as an additive to coat the layer of mesh to ensure development of an interconnected pore network.

In another aspect, wherein growing a biological matrix around the layer of mesh further comprises an act of sequentially seeding three different types of cells on the layer of mesh. In sequentially seeding three different types of cells on the layer of mesh, the three different types of cells are smooth muscle cells, fibroblast/myofibroblast cells, and endothelial cells. Further, protein, including TGF-β1, can be added to the collagen in each layer. Thus, as described above, the present invention is directed to a scaffold and various methods for forming such a scaffold.

BRIEF DESCRIPTION OF THE DRAWINGS

The objects, features and advantages of the present invention will be apparent from the following detailed descriptions of the preferred aspect of the invention in conjunction with reference to the following drawings where:

FIG. 3A is an image of a stainless steel mesh with a surface area of about 1 cm.sup.2;

FIG. 3B is a view of the engineered tissue after three months of cell culture;

FIG. 5A is a scanning electron microscopy image taken after culturing the second layer of cells containing fibroblasts and myofibroblasts;

FIG. 5B shows the formation of extracellular matrix and a layer of cells formed on the metal mesh, the black arrow indicates a single fibroblast cell;

FIG. 7A is a scanning electron microscopy image that show layers of tissue tightly enclosing the stainless steel mesh;

FIG. 7B is a scanning electron microscopy image that show three layers of tissue tightly enclosing the stainless steel mesh;

FIG. 7C is a scanning electron microscopy image that show three layers of tissue tightly enclosing the stainless steel mesh;

FIG. 7D is a scanning electron microscopy image that show three layers of tissue tightly enclosing the stainless steel mesh;

FIG. 9A is an illustration of a heart valve depicting the Nitinol mesh scaffolding;

FIG. 9B is an illustration of a heart valve with heart leaflets that are made of tissue described in this application;

FIG. 9C is an illustration of a heart valve with heart leaflets that are made of tissue described in this application;

FIG. 10A is a schematic representation of a blood vessel; and

FIG. 10B is a schematic representation of a blood vessel formed from the tissue described in this application.

DETAILED DESCRIPTION OF THE INVENTION

Figure 1B:
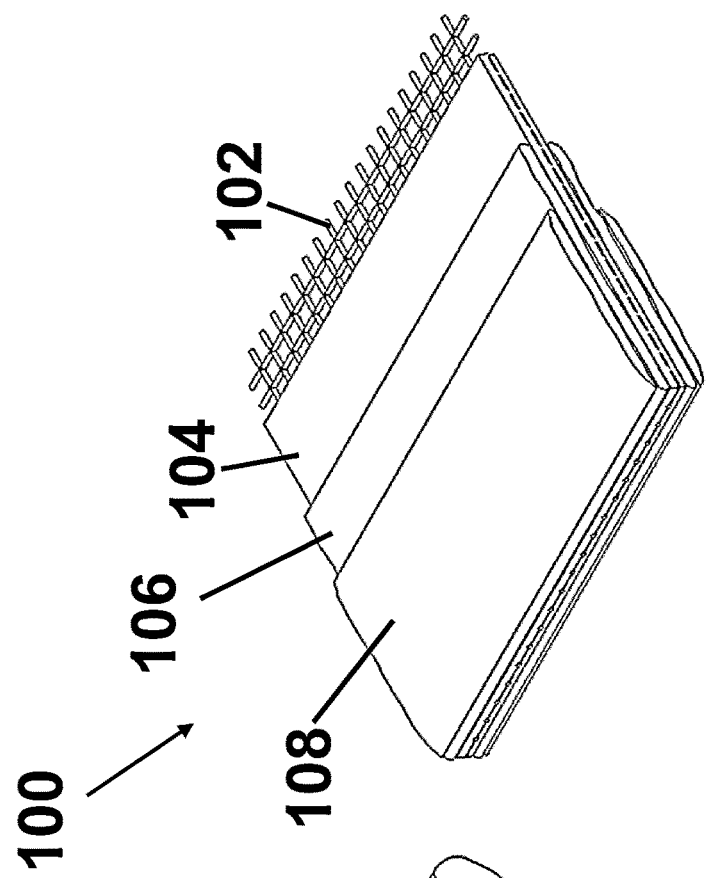
FIG. 1B is a diagram showing the three layers of cells of a scaffold that mimic heart valve tissue structure of one aspect of the present invention.

Reference will now be made in detail to embodiments of the present invention, examples of which are illustrated in the accompanying drawings. While the invention will be described in conjunction with these embodiments, it will be understood that they are not intended to limit the invention to these embodiments. On the contrary, the invention is intended to cover alternatives, modifications, and equivalents, which may be included with the spirit and scope of the invention as defined by the appended claims. Furthermore, in the following detailed description of embodiments of the present invention, numerous specific details are set forth in order to provide thorough understanding of the present invention. However, if will be recognized by one of ordinary skill in the art that the present invention may be practiced without these specific details. In other instances, well-known methods, procedures, and components have not been described in detail as not to unnecessarily obscure aspects of the embodiments of the present invention.

As noted above and as shown in FIG. 1A, the present invention is directed to a scaffold 100 that is composed of multi-layered tissue enclosed on a metal mesh. This is further illustrated in FIG. 1B, which illustrates that the scaffold 100 is made of an extra layer of metal mesh 102 enclosed by a biological matrix, such as layers (e.g., three layers) of cells (e.g., different cell types). It should be understood that while the present invention is described as scaffold 100 that includes three layers of different cell types, it is not intended to be limited thereto as the scaffold 100 can be formed with a single layer, or any suitable number of layers, and, further, with a single or different cell types. Additionally, while the mesh 102 is described as being covered with biological materials or a biological matrix, the invention is not limited thereto as the mesh 102 can also be enclosed by synthetic materials that are known to one skilled in the art (such as polymers, etc.) As a non-limiting example, the synthetic material can be molded onto the mesh.

However, desirably, the three layers of biological materials include a first layer 104 of smooth muscle cells. The second layer 106 may be composed of fibroblast and myofibroblast cells and the third layer 108 (which can is the outer layer) may comprise of endothelial cells. These three layers wrap around the metal mesh 102 in three-dimensions so that each layer fully envelopes the metal mesh 102. This approach is intended to retain all the advantages of using biological scaffolds while developing a strong extracellular matrix (ECM) backbone composed of the mesh 102 that can withstand various types of loads after implantation inside the body. Additionally, such a mesh pattern ensures structure integration of the formed tissue and allows cells and ECM components on both sides of the mesh 102 to interact with each other. The formed tissue is intended to be biomechanically resilient against the physiological stresses inside the body. In one aspect, the scaffold 100 is a living tissue, able to continually remodel and mature in vitro and in vivo. For example, the scaffold 100 has living tissue (as described below) that can continue to grow and mature, with the mesh 102 becoming biologically active when implanted in-vivo.

In one aspect, the three layers of cells of the scaffold 100 may mimic the heart valve structure. These three layers mimic ventricularis, spongiosa and fibrosa layers of a heart valve leaflet. This type of scaffold can be used in any membrane tissue fabrication, such as heart valve leaflets, vascular grafts, etc.

Figure 1A:
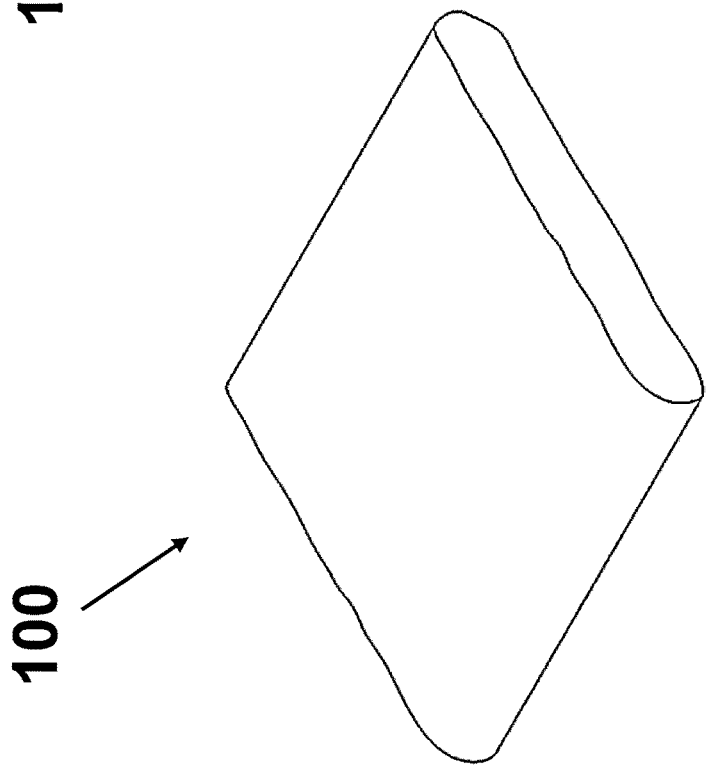
FIG. 1A shows a representation of a scaffold of one aspect of the present invention.
Figure 2:
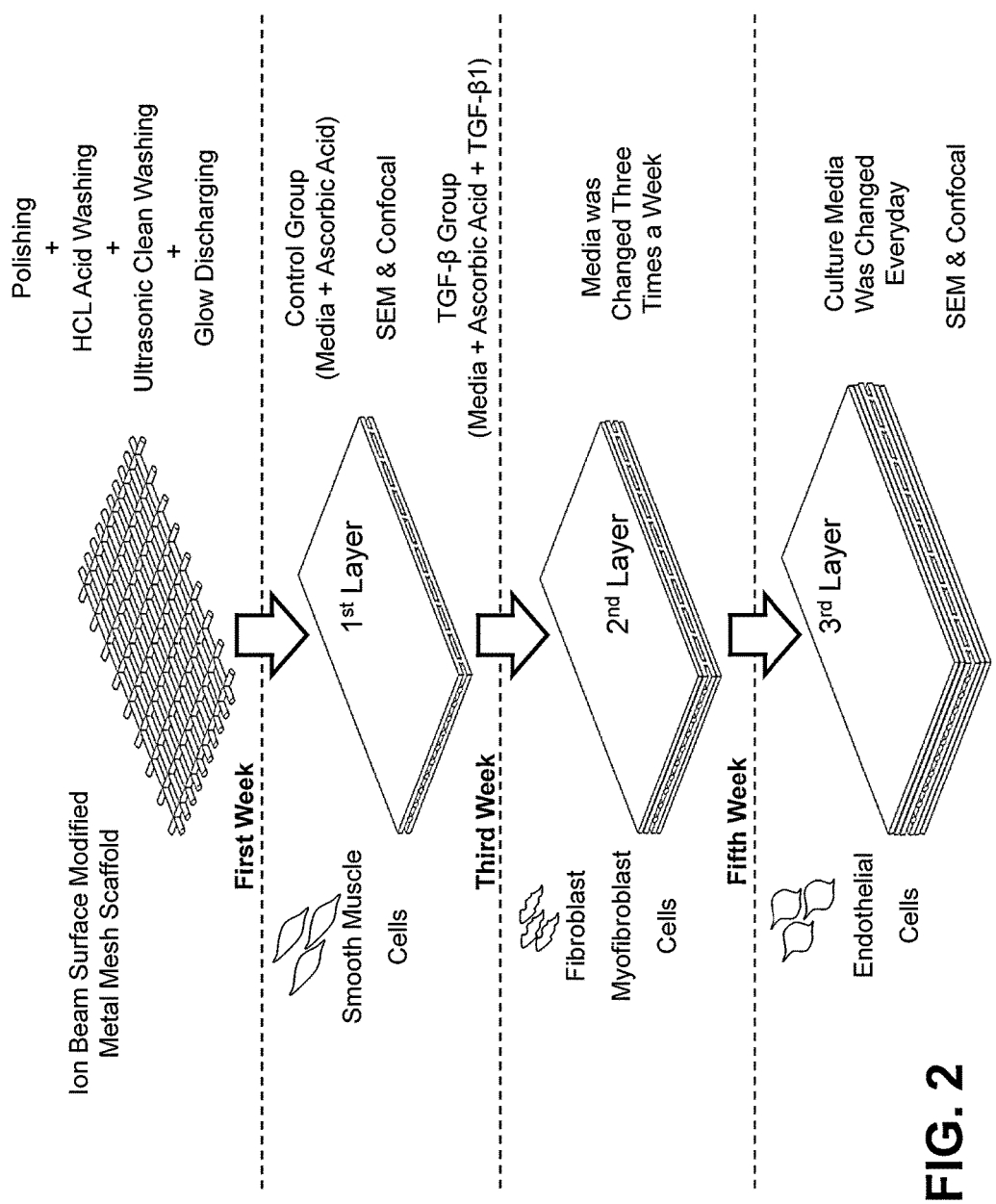
FIG. 2 is a schematic showing the steps in the three-dimensional (3D) cell culture method to develop a tissue.

While the present invention is directed to a unique hybrid scaffold 100 as shown in FIGS. 1A and 1B, the present invention also includes the method of making the novel scaffold (made of an extra layer of metal mesh enclosed by three layers of different cell types). For example, FIG. 2 shows a schematic diagram of a method for producing the multilayered tissue. Through the three-dimensional cell culture technique detailed in this application, all layers of the cells were seeded on rectangular-shaped Stainless Steel meshes to produce ECM or connective tissue.

The method of making the multilayered tissue is as follows. The first step in creating the scaffold is preparation of the metal mesh scaffold. The metal mesh is any suitable material that can operate as scaffolding for a tissue. As a non-limiting example, the metal mesh may be a flat mesh of T316 Stainless Steel woven from 0.0037" round wires, targeting at 80 end per inch (EPI)×80 pick per inch (PPI) that possesses an opening size of 0.0088". A non-limiting example of such a mesh is that sold by TWP, Inc., located at 2831 Tenth Street, Berkeley, Calif. 94710 USA. The metal mesh was heated at 520° C. for 5 min, followed by water quenching. The oxidized film was removed at multiple stages; by polishing the surface, using hydrochloric acid wash, ultrasonic cleaning wash in ethanol for 15 min and glow discharging for 40 seconds. Finally, the mesh was cut into pieces with area of one square centimeter to be used for cell culture.

After the metal was cleaned and cut into pieces, an ion beam surface modification method was used to get a smooth surface and ensure the biocompatibility and enhanced cell attachment for the Stainless Steel meshes. The meshes were mechanically polished with wetted metallographic polishing high-grade Silicon Carbide (SiC) papers. Afterward, the meshes were acid-washed, degreased in an ultrasonic vibrobath, and rinsed with distilled water. Prior to cell culture, the samples were irradiated by $He^+$ ion beam at energy of 150 keV with fluences of $1 \times 10^{14}$ ions/cm$^2$.

In one aspect, the growth of the tissue may be aided by the addition of growth factors and materials. For example, a mixture containing bovine and rat tail collagen may be used to coat the mesh to ensure development of an interconnected pore network, which is essential for cell growth, nutrient supply, and removal of metabolic waste products. In addition, the culture media may be supplemented with additives, including, but not limited to, ascorbic acid to promote matrix production. Moreover, proteins (cytokines), including TGF-β1, may be added to the collagen gels in each layer to increase the rate of extracellular matrix production. For the biological part of the scaffold any collagen type by itself or in mixture as well as the other biological scaffold such as fibrin or even synthetic scaffolds can be used. Growth factors depending on the target tissue and the cells that have been used can be different, such as vascular endothelial growth factor (VEGF) if endothelial progenitor cells are used instead of endothelial cells.

After the mesh has been prepared, the three-dimensional tissue scaffold was constructed by sequential seeding of three different types of cells on the metal mesh. As a non-limiting example, three different cell types were isolated and used for preliminary assay, as follows: smooth muscle cells and fibroblast and myofibroblast cells to fulfill the role of valvular interstitial cells (VICs) and endothelial cells to act as the valvular endothelial cells. The basal media for culturing cells contained DMEM (e.g., Dulbecco's Modified Eagle Medium, Gibco, produced by Invitrogen Corporation, located at 1600 Faraday Ave., Carlsbad, Calif. 92006, USA), 10% fetal bovine serum (HyClone, Rockford, Ill.), 1% penicillin/streptomycin (Gibco, Carlsbad, Calif.) and 1% L-glutamine (Gibco, Carlsbad, Calif.), with appropriate growth factors added to it for enhancement of growth and proliferation. Cultured cells were fed every two to three days, and split 1 to 3 at confluence. Cells were used on the passages 3 to 5 for the experiment.

Each mesh was coated with a mixture of bovine and rat tail collagen (Gibco, Carlsbad, Calif.) in a tissue culture hood with an aligned appearance. The liquid collagen mixture was neutralized using NaOH. Cell-seeded collagen constructs were prepared by first casting an acellular collagen solution and then adding a total of $3 \times 10^6$ cells for each cell type to it, before the collagen had set. After placing the Stainless Steel meshes among the solutions, the constructs were incubated at 37° C. in a 5% $CO_2$ humidified incubator for polymerization. This method ensures that collagen constructs have uniform cell density ($3 \times 10^6$ cells/cm$^2$) after gel formation. The tissue constructs were cultured at 37° C. with replacement of culture media every two days. To achieve a phenotype similar to the natural valve leaflets in-vivo, the cells in the next layers were plated over the constructs at time intervals of two weeks and the next layer was constructed around the deeper layer in a similar method that has been described in the beginning of this paragraph. The media was also supplemented with ascorbic acid (e.g., produced by Sigma-Aldrich Inc., located at 3050 Spruce Street, St. Louis, Mo. 63103, USA) as an additive to promote matrix production. To increase the rate of extracellular matrix production, 10 ng/ml of TGF-β1 (e.g., produced by R&D Systems Inc., located at 614 McKinley Place Northeast, Minneapolis, Minn. 55413, USA) was added to the collagen gels in each layer. These cultures were later on compared to the control group with no TGF-β supplementation.

In one aspect, the tissue may be suitable for applications in which strong composition of the membrane is essential, including but not limited to, heart valves and vascular grafts. For further understanding, FIGS. 3A and 3B provide images that depict the scale and size of the mesh and corresponding tissue. For example, FIG. 3A is an image of a stainless steel mesh 102 with a surface area of about one square centimeter Additionally, FIG. 3B is a macroscopic view of the engineered tissue 100 after three months of cell culture. The outer surface shown in FIG. 3B is the endothelial layer or the third layer. Seeding the third layer completely concealed the mesh 102 and formed a smooth, confluent surface around the construct. Although the third layer concealed the mesh 102, the metallic mesh 102 can still be seen inside the tissue.

Figures 4A, 4B:
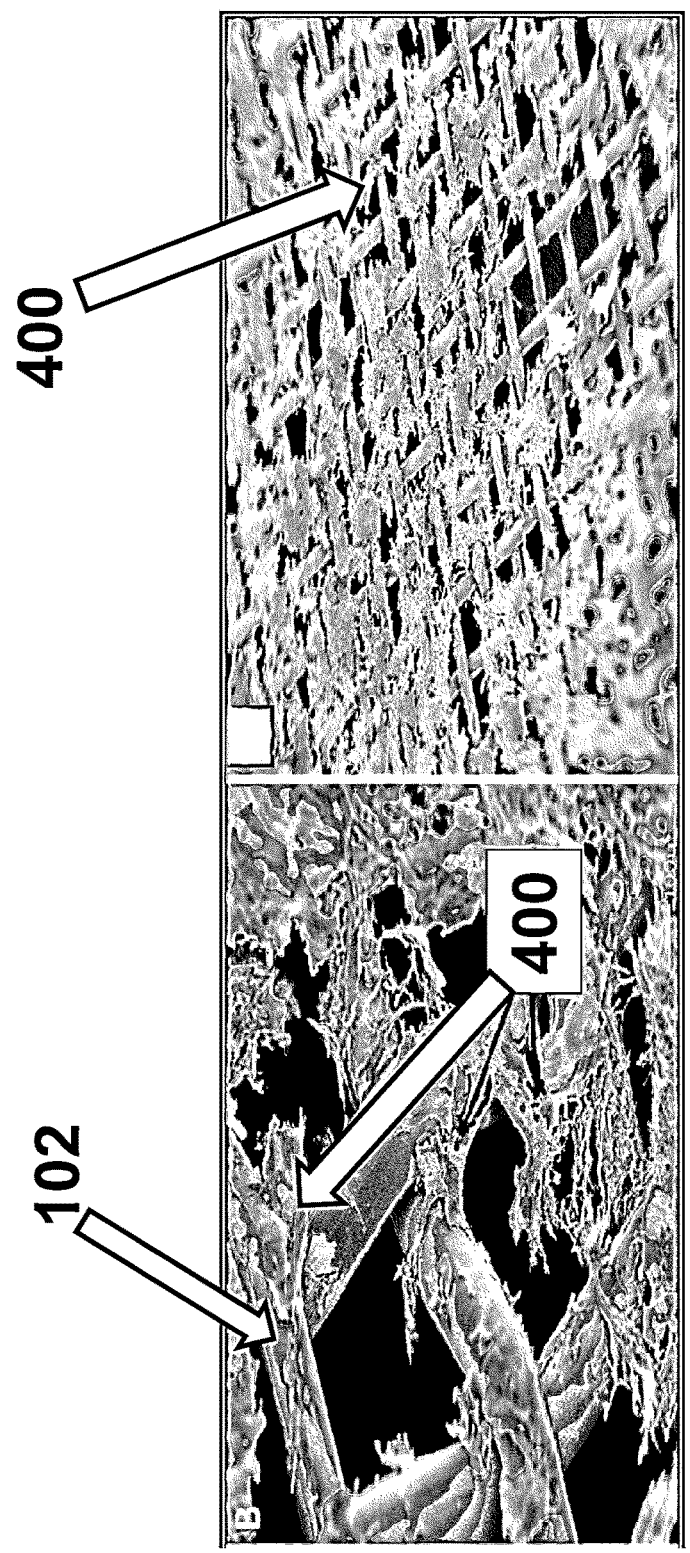
FIG. 4A is a scanning electron micrograph of the first layer on the mesh showing that smooth muscle cells are attached over the mesh.
FIG. 4B is a expanded view of FIG. 4A.

FIG. 4A and FIG. 4B are scanning electron micrographs (SEM) images of the first layer of cells. FIG. 4A shows the smooth muscle cells 400 as being attached over the mesh 102. FIG. 4B shows the first layer of tissue (i.e., the smooth muscle cells 400) compacted during the culture period, which confirmed the expression of alpha-SMA, as its expression.

FIG. 5A is a top-view of the SEM image taken after culturing the second layer of cells containing fibroblasts/myofibroblasts. Formation of ECM and a confluent layer around the construct are visible. Alternatively, FIG. 5B shows a side-view of the SEM image. The arrow in FIG. 5B indicates a single fibroblast cell 500. Both FIG. 5A and FIG. 5B show fibroblast cells 500 in the second layer. Addition of TGF-β increased the number of cells with either fibroblasts or myofibroblasts in the second layer.

Figure 6A:
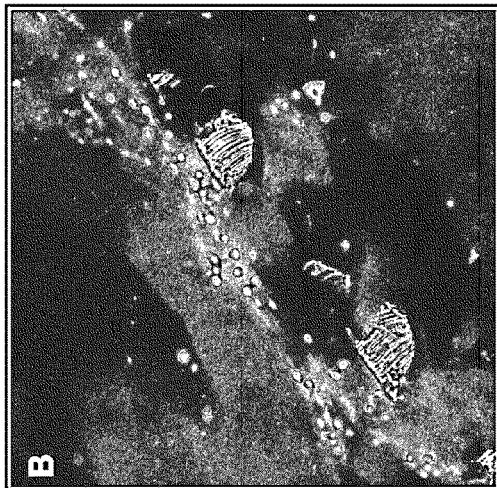
FIG. 6A shows a top view of cell culture without addition of TGF-β.
Figure 6B:
FIG. 6B shows a top view of cell culture without addition of TGF-β.
Figure 6C:
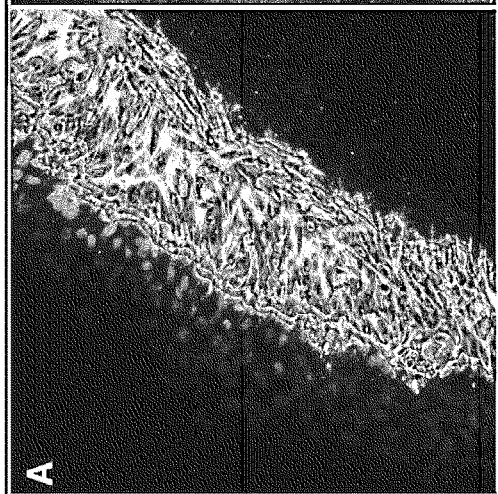
FIG. 6C shows the top view of the cell culture with TGF-β added to the cell culture.
Figure 6D:
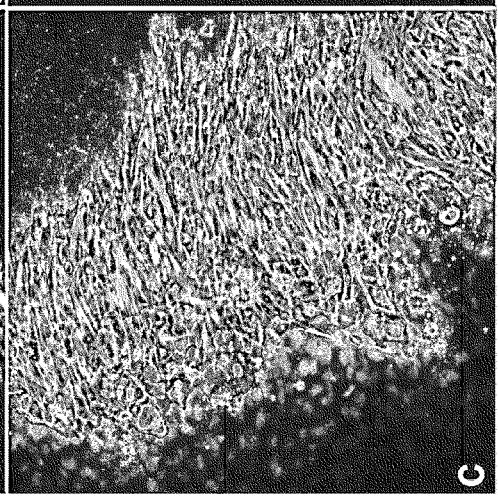
FIG. 6D shows the top view of the cell culture with TGF-β added to the cell culture.

FIGS. 6A through FIG. 6D show confocal microscopy images of the cell culture at the end of the eighth week, with and without addition of TGF-β. FIG. 6A shows the control group from a top-view, without TGF-β added. FIG. 6B shows the control group from a side-view without TGF-β added. Alternatively, FIG. 6C is a top-view image of the cell culture with TGF-β added to the cell culture. FIG. 6D is a side-view image, showing the cell culture with TGF-β added to the cell culture. As shown between FIGS. 6A through 6D, greater extracellular matrix deposition is observed when TGF-β is added, in comparison to control groups. DAPI (i.e., 4',6-Diamidino-2-Phenylindole, Dihydrochloride) staining of nuclei in the construct shows that the number of cells at the surface of the mesh increased progressively in TGF-β groups, and the groups treated with TGF-β eventually formed a thicker tissue around the mesh.

FIGS. 7A through 7D show SEM images taken after eight weeks, depicting the three layers of tissue tightly enclosing the stainless steel mesh. FIG. 7A shows the endothelial surface layer 108, the smooth structures covering the construct in a confluent manner. FIG. 7B shows that after eight weeks, the tissue shows three different cell layers in sequence, 108 is the surface endothelial layer, 106 is the middle fibroblast and myofibroblast layer, and 104 is the base layer of smooth muscle cells. FIG. 7C and FIG. 7D show that the mesh 102 is tightly integrated with the tissue membrane, with FIG. 7C further illustrating that the cells 104 are penetrating through the mesh 102 opening holes. It can be observed that adding the second and the third layers improves production of the ECM (mainly collagen and glycosaminoglycans) that covers the mesh, forming a confluent smooth surface with endothelial cell lining in both experimental groups.

Figures 8A, 8B:
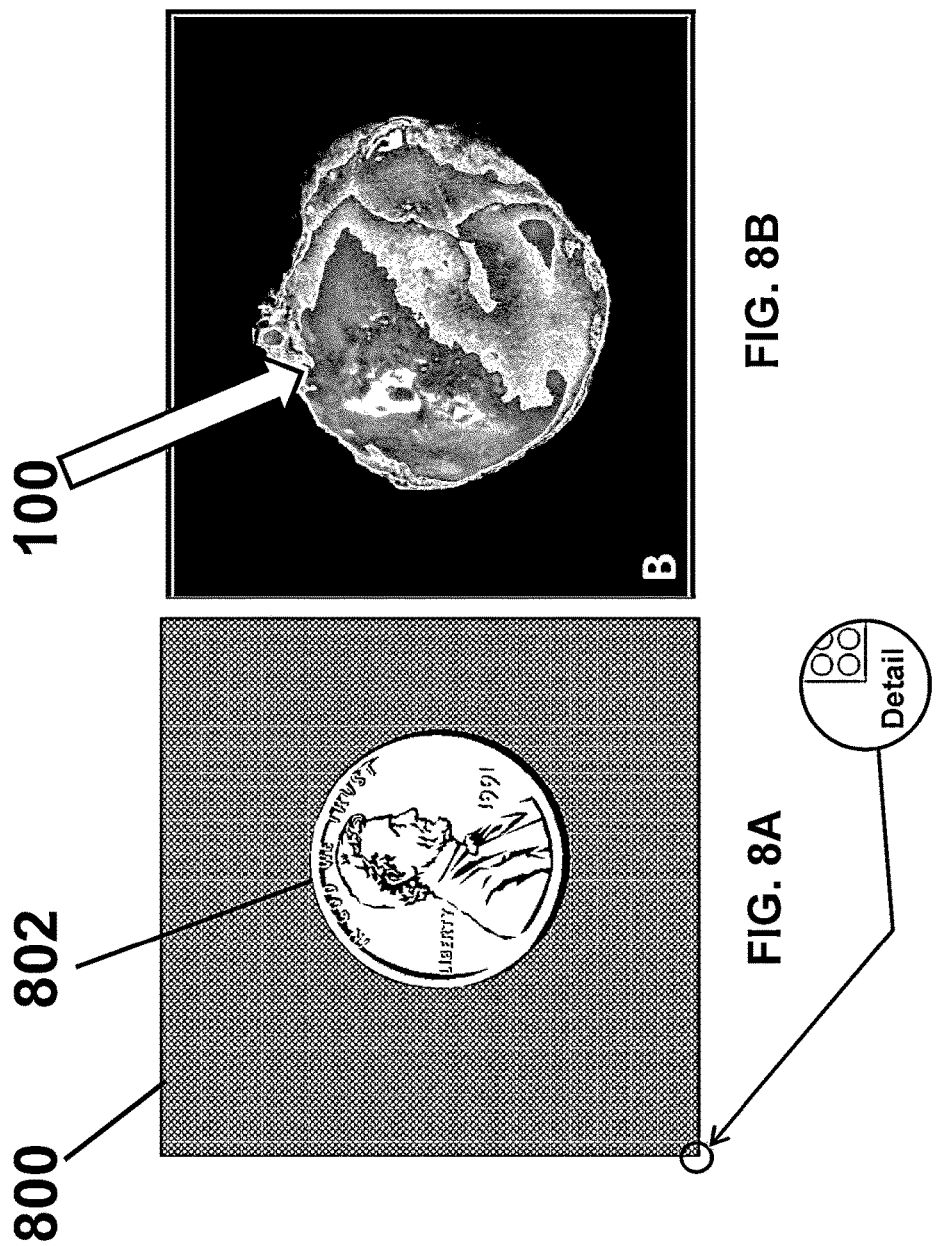
FIG. 8A is an illustration depicting a size comparison of a one-centimeter by one-centimeter Nitinol mesh in relation to a United States Penny.
FIG. 8B shows the engineered tissue on Nitinol mesh after the months of cell culture.

As noted above, the metal mesh is any suitable material that can operate as scaffolding for a tissue. Further, the mesh can be in any form, non-limiting examples of which include being braided or flat (e.g., the mesh is fabricated as sheet of punched wire mesh or with a woven pattern). In another aspect, a Nitinol metal mesh scaffold may be used instead of stainless steel metal mesh for the scaffold. For scale comparison, FIG. 8A shows multiple sheets of one centimeter by one centimer Nitinol mesh 800 in relation to a United States one cent coin 802. In production of the tissue, the Nitinol metal mesh 800 is etched with acid in the same process used for the Stainless Steel metal mesh. In this non-limiting example, the mesh 800 is made of a superelastic Nitinol sheet with the thickness of 76 microns etched as a network of holes with 240 microns diameter and the central distance of 320 microns. For the heart valve leaflet application, a sheet that is 25 microns thick is used, which provides the desired elastic recoil of the leaflets. In this aspect, the mesh 800 is cut to the shape of a heart valve leaflet. The Nitinol mesh is seeded with cells in the same manner as the described for the Stainless Steel mesh. An example of the resulting scaffold 100 that is grown for 3 months is shown in FIG. 8B.

As noted above, the scaffold of the present invention can be incorporated into any suitable tissue based item, a non-limiting example of which includes a vascular graft. As another non-limiting example and as shown in FIGS. 9A through 9C, the scaffold may be incorporated into a tissue heart valve that mimics the natural heart valve. The tissue heart valve comprises a flexible frame having a saddle-shaped base 901 and at least two upstanding posts 902 (or three as depicted), which divide the base into at least two portions (or three as depicted), together with tissue leaflets 903 formed from the tissue described in this application. The posts 902 can be formed at opposite ends of a diameter of an undistorted base or, as depicted three (or more) posts 902 are placed at regular intervals around the base.

The tissue leaflets 903 each having a periphery consisting of a free portion 906 extending between the tips of posts 902 and a fixed portion secured, sealed or sutured to corresponding sides of the posts 902 and the adjacent portion of the base 901. The leaflets 903 are made of a mesh material, such as but not limited to superelastic Nitinol mesh (or Stainless Steel or any other suitable mesh material). The superelastic mesh acts as a structure that defines the shape of the leaflets 903 and can be a structure, such as but not limited to a mesh with arranged or unarranged holes. The mesh can be fabricated, such as but not limited to a sheet of punched wire mesh or with a woven pattern.

To use the heart valve shown in FIGS. 9A through 9C, the saddle-shaped base 901 is attached to the circumference of the auriculoventricular orifice, preferably through an intermediate suture ring 904, whereby the base can deform from a substantially circular shape to the shape of the orifice simultaneously, as is the case with the natural heart valve. In a valve replacement, the posts 902 may be disposed at regular intervals round the undistorted base, or at other intervals as needed, for example, by the anatomical requirements of coronary ostia in aortic valve replacement.

The flexible frame (i.e., saddle-shaped base 901 and at least two upstanding posts 902) is formed of any suitably flexible yet durable material. As a non-limiting example, the flexible frame is desirably formed of ELGILOY®, a Co—Cr—Ni alloy, covered with a woven polyester cloth 912 (such as but not limited to DACRON® cloth, or any other suitable covering material), with the differential flexibility afforded by differing thicknesses of the frame material to either side of the posts and/or differing thicknesses of ELGILOY® at each portion of the posts. It is designed to be compliant at the orifice and commissures to reduce the closing loading shocks at the commissure tips and free margin of the leaflets. The suture ring 904 can contain inserts of silicone rubber and non-woven polyester. At least two contrasting marking sutures 905 are located on the suture ring 904. The marking sutures 905 are intended to aid in the proper orientation for implanting the prosthesis. The posts 902 desirably merge at each side into the respective arcuate portions of the saddle-shaped base 901, with the merging preferably being by way of a continuous curve from the rounded tip of one post 902 to the rounded tip of the other post 902.

For example in a tri-leaflet valve, the shape of each leaflet 903 preferably corresponds to a portion of a surface of a cone, which portion is defined by the intersections on the conical surface of three flat planes with sixty degree angles together. The three flat panes having peripheries on the conical surface corresponding in length respectively to the circumference of the saddle-shaped base and the distance between the tips of the posts of the frame. A forth intersection is included on the conical surface of a curved plane that is concave towards the apex of the cone and intersects the three mentioned flat planes at opposite sides of the cone. The spacing of the flat planes and the curvature of the curved plane are such that the development of the curved plane on the conical surface matches in length and curvature a continuously blending of the curve of one arcuate portion of the saddle-shaped base and the adjacent sides of the posts, so that no moulding or stress-fixing of the leaflet material is required.

For further understanding of the scaffold nature of the heart valve, FIG. 9A depicts the heart valve with the mesh (such as Nitinol mesh 800) that is the underlying base structure of the leaflets 903. Specifically, FIG. 9A illustrates the heart valve and its scaffold without the biological matrix. FIG. 9A includes an enlarged view 910 of the Nitinol mesh 800 to illustrate a non-limiting example of a mesh pattern and the holes therethrough. Further, as shown in FIG. 9B, the three layers are grown on top of the Nitinol mesh 800. Specifically, shown is the first layer 104 of smooth muscle cells, the second layer 106 of fibroblast and myofibroblast cells and the third layer 108 of endothelial cells. Finally, FIG. 9C illustrates a resulting heart valve, where the outer layer of each leaflet 903 is the third layer 108 (or endothelial cells).

Figure 9D:
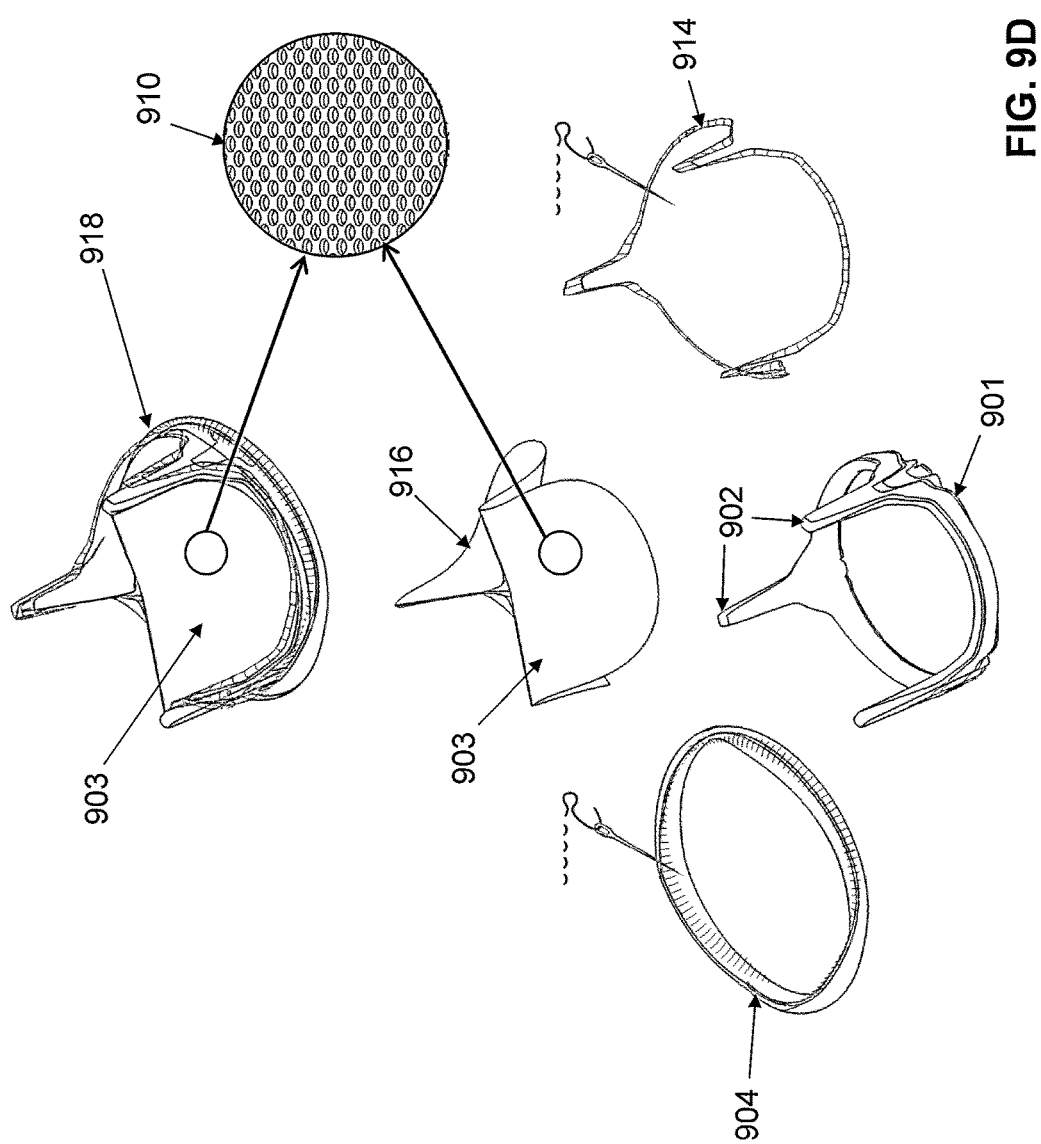
FIG. 9D is an illustration depicting schematic parts of a tri-leaflet scaffold that can be used as a heart valve.

For further understanding of a suitable base structure, FIG. 9D illustrates components of the heart valve as depicted in FIG. 9A. Shown in FIG. 9D is the flexible frame that includes the saddle-shaped base 901 and at least two upstanding posts 902. The suture ring 904 is also depicted in FIG. 9D, along with the suture material 914. Further, the leaflets 903 are shown, including an enlarged view 910 of the mesh to illustrate an example of the mesh pattern.

Figure 9E:
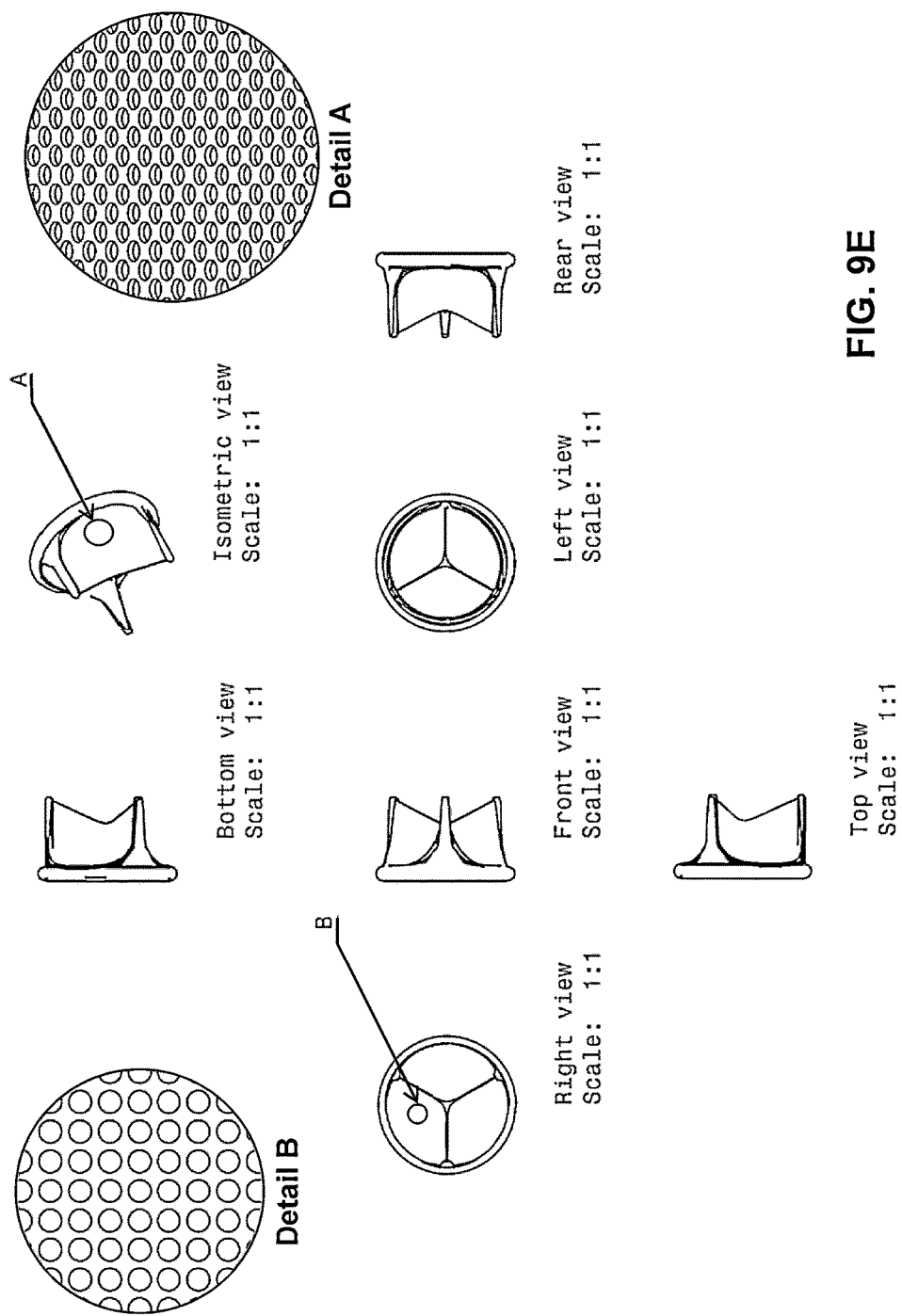
FIG. 9E is an illustration that includes various view-point illustrations of the heart valve.
Figure 9F:
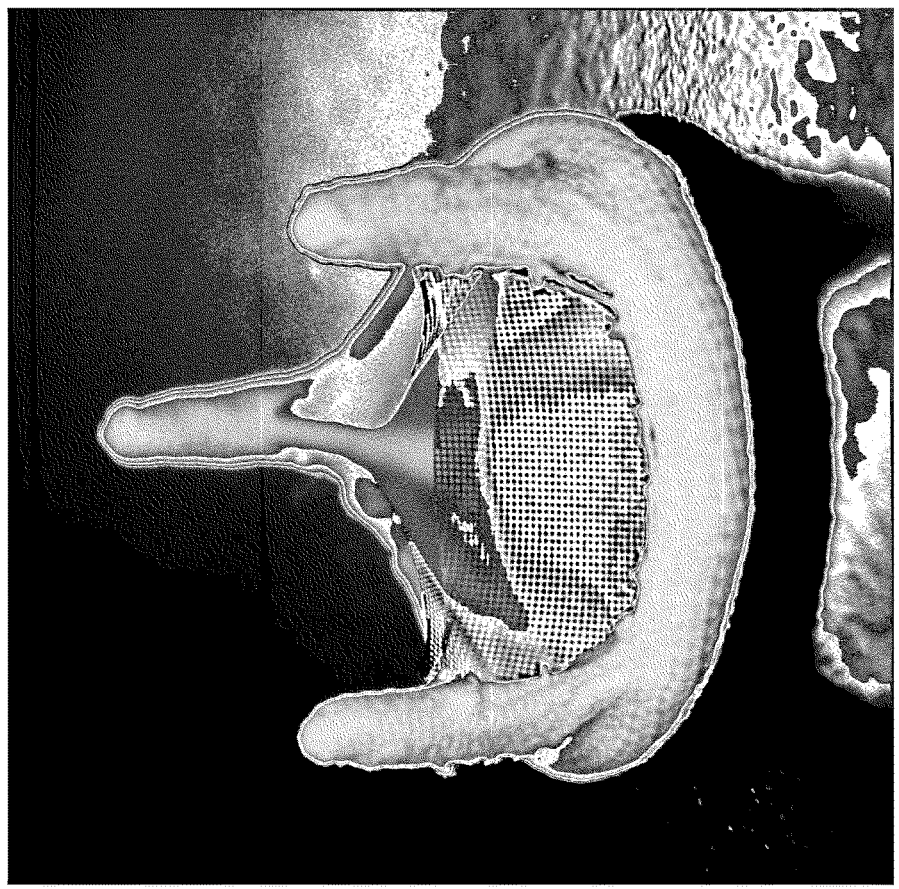
FIG. 9F is an image of the tri-leaflet scaffold that is depicted in FIGS. 9A and 9D.

As shown, the leaflets 903 can be attached together to form a dimensionally stable and consistent coating leaflet subassembly 916 when subjected to physiological pressures. Then each of the leaflets 903 of the subassembly 916 is aligned with and individually sewn to the frame (i.e., the saddle-shaped base 901 and posts 902), typically from one commissure tip (i.e., post 902), uniformly around the leaflet 903 cusp perimeter, to the tip of an adjacent commissure tip (post 902). The frame (base 901 and 902) is usually covered with cloth but can alternatively be covered with biologic tissue. The sewed sutures 914 act like similarly aligned staples, all of which equally take toe loading force acting along the entire cusp of each of the pre-aligned leaflets 903. The resulting structural assembly (i.e., the heart valve 918 depicted at the top of FIG. 9D and also shown in FIG. 9A) thereby formed reduces stress and potential fatigue at the leaflet suture interface by distributing stress evenly over the entire leaflet cusp from commissure to commissure. Thus, unlike some bioprosthetic valves wherein leaflets are attached individually and the peripheral stitching of the cusps terminates before the tips of the commissures, producing a potential stress point, the produced valve assembly has uniform stitching from commissure tip to commissure tip and consistently aligned coapting leaflet mating edges. This is further illustrated in FIG. 9E, which provides various view-point illustrations of the tri-leaflet heart valve to clearly illustrate the shape of the valve assembly (i.e., tri-leaflet heart valve) and its leaflet mating edges. Finally and for further illustration, FIG. 9F provides an illustration of the tri-leaflet scaffold that is depicted in FIGS. 9A and 9D.

FIG. 10A and FIG. 10B provide yet another example of a tissue based item that can be adapted or formed to incorporate the scaffold. For example, FIG. 10A is a schematic representation of a blood vessel, depicting the various components of an actual blood vessel. Alternatively, FIG. 10B illustrates the scaffold formed as a blood vessel. As shown, the scaffold in this example includes the base Nitinol mesh 800 that is provided in a tubular wire mesh form to mimic the shape of a blood vessel. The corresponding tissue is grown around the Nitinol mesh 800. Thus, as can be appreciated, the present invention enables for the generation of a variety of scaffolds that are strong enough to resist forces that exist inside a body, while possessing biocompatible surfaces.

Mesh Made Heart Valves

Some embodiments relate to development of a heart valve, whose leaflets are made of a mesh material.

Valvular heart disease is one of the most common causes of heart problems and is associated with high mortality. Treatment for severe cases is valve replacement or valve repair. Over 260,000 replacement procedures are performed each year worldwide. Two types of valves are currently used: mechanical and bioprosthetic (tissue). Mechanical valves are recommended for patients aged 15-64 because they are durable; however, they significantly increase the risk of blood clot formation and require patients to be on lifelong anticoagulation medication, which increases the likelihood of life-threatening bleeding episodes. Bioprosthetic valves, on the other hand, are biocompatible and do not require the use of anticoagulants. However, they last on average only 15-20 years, with 30% of patients requiring reoperation within the first 10 years. This is not as significant for the cohort that is 65 and older, since they have a shorter life expectancy, but is problematic for younger patients because health risks increase with each reoperation. Clearly, there is a need for a valve that solves both the issue of biocompatibility and durability for patients.

In some embodiments, the mesh material is a polymer, such as a surgical mesh. Biocompatibility of polymer mesh implants is good. For example, polyvinylidene fluoride (PVDF, PRONOVA™) is a non-absorbable polymer which features superior textile and biostable properties. Compared to polyester, it shows a higher mechanical stability. In addition, progression of rigidity is not an issue, for example as seen with polypropylene. PVDF is an advantageous alternative to other commonly used materials due to an improved biostability and biocompatibility.

In some embodiments, the mesh material is a metal, such as but not limited to superelastic Nitinol material. For example, titanium and titanium alloys offer desirable properties, such as relatively low modulus, good fatigue strength, formability, machinability, corrosion resistance, and biocompatibility. Some embodiments may include a stainless steel mesh. Metal mesh materials may optionally contain a combination of biocompatible metals or be used in conjunction with other biomaterials.

As used herein, "biocompatible metal or biocompatible alloy" is defined as individual metals or metal combinations (alloy). An example of a biocompatible metal is pure titanium or pure zirconium with any additional metals less than 1 wt %. Examples of biocompatible alloys include cobalt-chromium-molybdenum, titanium-aluminum-vanadium, nickel-titanium and zirconium-niobium. Other biocompatible alloys may be made from either zirconium or titanium or tantalum or niobium or hafnium or combinations thereof.

Nitinol is a commonly used metal. Nitinol, which is formed by alloying nickel and titanium (~50% Ni), is a shape memory alloy with superelastic properties similar to that of bone, in comparison to stainless steel (another commonly used biomaterial). This property makes nitinol an especially advantageous material for biomedical applications.

In some embodiments, the mesh material has openings or holes that enable capture of circulatory/stationary/migratory cells, and minimize the effect of the metal on in vivo formed tissue natural remodeling. In some embodiments, the hole openings have a diameter (in inches) of about 0.0005, 0.0010, 0.0020, 0.0030, 0.0040, 0.0050, 0.0060, 0.0070, 0.0080, 0.0088, 0.0090, 0.0100, 0.110, 0.0120, 0.0130, 0.0140, 0.0150, 0.0160, 0.0170, 0.0180, 0.0190, or 0.0200.

In some embodiments, the mesh material has a thickness (in inches) of about 0.0004, 0.0005, 0.0006, 0.0007, 0.0008, 0.0009, 0.0010, 0.0015, 0.0020, 0.0025, 0.0030, 0.0035, 0.0040, 0.0045, 0.0050, 0.0055, 0.0060, 0.0065, 0.0070, 0.0075, 0.0080, 0.0085, 0.0090, 0.0095 or 0.0100.

Surprisingly, the inventors have discovered that heart valve leaflets containing these hole dimensions and thickness demonstrate functional properties very similar to native heart valve leaflets, even in the absence of cells growing on the surface of the mesh. Although the heart valve leaflets contain numerous holes that pass through the mesh, the fluid dynamics of a prosthetic heart valve containing such leaflets are comparable to a native heart valve. Moreover, the flexibility of metal meshes having these dimensions minimizes tissue detachment, clotting or excessive tissue growth.

Surface Modification with Bioactive Materials

With respect to the heart valve leaflets disclosed herein, various types of bioactive materials can be used to optimize cell capture, as wells as to promote active recruitment and to provide differentiation guidance.

A mesh used in a heart valve leaflet may be modified to contain a molecule that interacts with a cell adhesion molecule. Cell adhesion molecules (CAMs) are proteins located on a cell surface involved in binding with other cells or with the extracellular matrix (ECM) in the process called cell adhesion. Two well-known examples are CD34 and GLYCAM-1. Any molecule that interacts with a cell adhesion molecule may be associated with a mesh, such as but not limited to a CD34 antibody or a GLYCAM-1 antibody. CD34 molecule is a cluster of differentiation molecule present on certain cells within the human body. It is a cell surface glycoprotein and functions as a cell-cell adhesion factor. Glycosylation-dependent cell adhesion molecule-1 (GLYCAM-1) is a proteoglycan ligand expressed on cells. Integrins, which are one of the major classes of receptors within the extracellular matrix (ECM), mediate cell-ECM interactions with collagen, fibrinogen, fibronectin, and vitronectin. Integrins provide essential links between the extracellular environment and the intracellular signalling pathways. Cadherins are homophilic $Ca^{2+}$-dependent glycoproteins, which link to the actin filament network through specific linking proteins called catenins. Many cell types express combinations of cadherin types. The extracellular domain has major repeats called extracellular cadherin domains (ECD). Selectins are a family of heterophilic CAMs that bind fucosylated carbohydrates, e.g., mucins. Three family members include E-selectin (endothelial), L-selectin (leukocyte), and P-selectin (platelet). A well characterized ligand for the three selectins is P-selectin glycoprotein ligand-1 (PSGL-1), a mucin-type glycoprotein expressed on white blood cells.

A mesh used in a heart valve leaflet may be modified to contain a molecule that interacts with a cellular receptor, such as a growth factor. Epidermal growth factor (EGF) is a growth factor that stimulates cell growth, proliferation, and differentiation by binding to its receptor EGFR. Fibroblast growth factors (FGFs) are a family of growth factors, with members involved in angiogenesis, wound healing, embryonic development and various endocrine signaling pathways. The mammalian fibroblast growth factor receptor family includes FGFR1, FGFR2, FGFR3, and FGFR4. Vascular endothelial growth factor (VEGF) is a signal protein produced by cells that stimulates vasculogenesis and angiogenesis. VEGFs include VEGF-A, VEGF-B, VEGF-C and VEGF-D, and placenta growth factor (PGF).

A mesh used in a heart valve leaflet may be modified to contain a subendothelial extracellular matrix molecule, such as fibulin-5 and fibrillin-1, or an extracellular matrix molecule.

A mesh used in a heart valve leaflet may be modified to contain a peptide-based coating, such as an RGD-peptide. Proteins that contain the Arg-Gly-Asp (RGD) attachment site, together with the integrins that serve as receptors for them, constitute a major recognition system for cell adhesion. The RGD sequence is the cell attachment site of a large number of adhesive extracellular matrix, blood, and cell surface proteins.

In some embodiments, a bioactive material is coated onto the surface of a mesh. Such coating may be carried out by: (a) providing a solution comprising a dissolved protein, (b) contacting the solution with a surface of a mesh, (c) allowing coating of the surface of said mesh with said dissolved protein, and (d) drying of the coated mesh obtained in step (c). In some embodiments, the mesh is a metal mesh.

Surface coating with a bioactive material may facilitate recruitment and/or binding of cells to the mesh due to an interaction between the bioactive material and various cell types, such as endothelial cells, smooth muscle cells and/or fibroblast/myoblast cells, for example by binding to a surface receptor on the cells.

In some embodiments, growth of cells on the mesh surface, for example, surface endothelialization, can prevent thrombogenicity. Nitinol alloy has been applied widely, due to its shape-memory property and superelastic capability.

When materials are introduced to the body, it is important not only that the material does not damage the body, but also that the environment of the body does not damage the implant. One method that prevents the negative effects resulting from this interaction is called passivation. Passivation is a process that removes corrosive implant elements from the implant-body interface and creates an oxide layer on the surface of the implant. The process can cause biomaterials to be more biocompatible. In some embodiments, a metal mesh surface is plasma coated, for example using a using a low-temperature plasma deposition technique.

In some embodiments, the surface of the metal mesh may be micropatterned, e.g., with mechanical polishing and/or chemical pickling to prepare surface topographies that enhance cell binding.

The disclosed mechanical valves retain adequate mechanical strength and durability similar to the current mechanical valves and they have excellent hemodynamic performance, no immunogenic, thrombogenic or inflammatory reactions. Therefore, there is no need for anticoagulation medication for the patients who use these types of valve. Moreover, the disclosed valves have the ability of capturing the circulatory/stationary/migratory cells of the body to become biologically active to self-growth, repair and remodel. The ability to capture circulatory/stationary/migratory cells of the body may be enhanced by modifying the surface of the valve leaflets, facilitating growth of a tissue layer on the mesh in a suitable environment (such as the body), so that the mesh may enclosed by the tissue layer.

Figure 11:
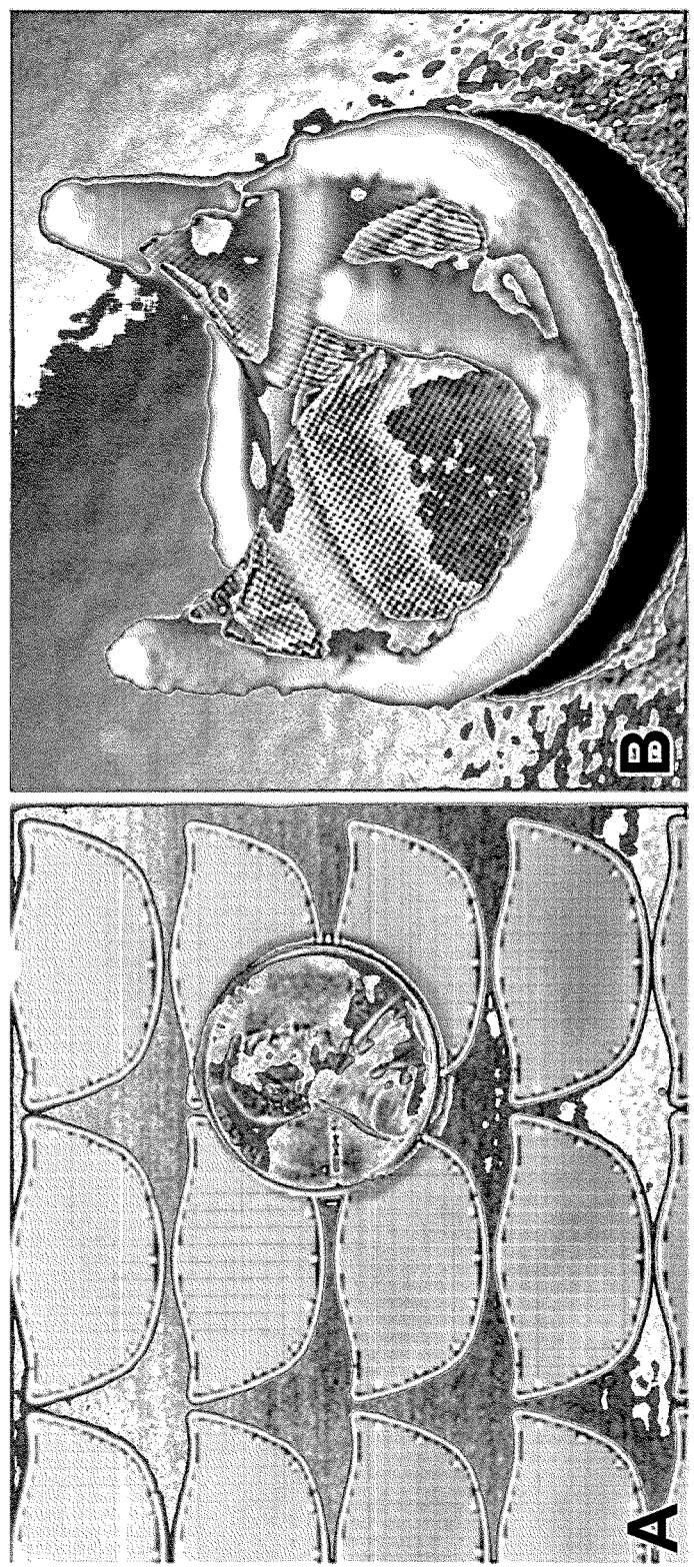
FIG. 11 depicts a Nitinol mesh leaflet and the bioactive valve. (A) The flat Nitinol mesh cut to the desired shape of a leaflet; (B) a tri-leaflet valve comprised of a stand, a base and leaflets made of 25 microns thickness Nitinol mesh leaflets, The surface of the mesh has been modified to becomes biologically active once implanted to capture the cells of the body.

Referring to FIG. 11, a bioactive heart valve replacement disclosed herein may comprise a flexible frame, similar to currently available bioprosthetic valves, and at least two upstanding posts, which divide the base into at least two portions, together with the mesh leaflets each having a periphery consisting of a free portion extending between the tips of posts and a fixed portion secured, sealed or sutured to corresponding sides of the posts and the adjacent portion of the base.

Once implanted, the heart valve may activate appropriate signaling cascades for cell recruitment and attachment in order to benefit from the body's natural regenerative ability. Currently available artificial heart valves have the disadvantage of lacking such signaling molecules and cannot offer biological functionality on their surface. Consequently, there has been a lot of research on the functional integration of bioactivity into biomaterials.

Figure 12:
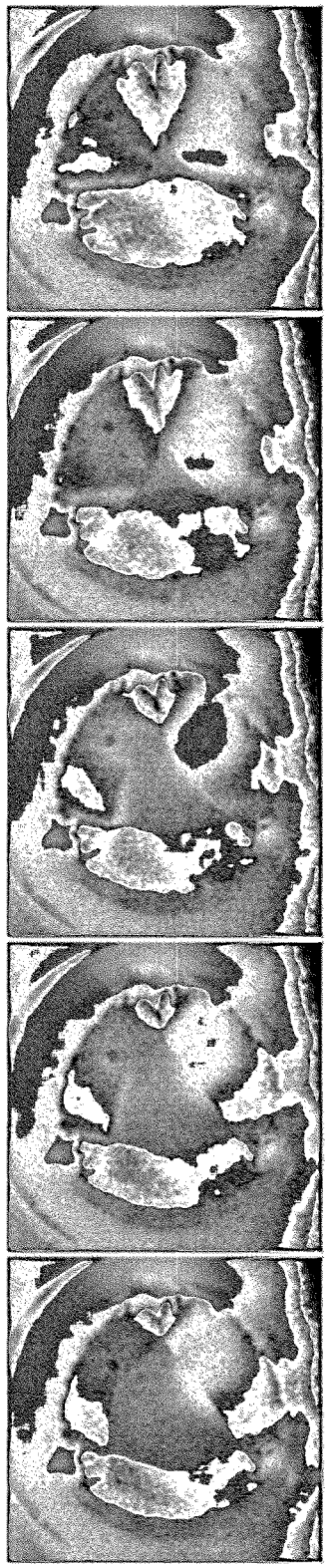
FIG. 12 depicts functional testing of a tri-leaflet bioactive valve with Nitinol mesh leaflets inside a heart flow simulator. The images are consecutive slides taken from a recorded movie showing opening and closure of the valve. It can be seen that the leaflets are compliant enough to open and close with a flow rate (3 L/min) even less than normal flow rate of the heart.

The compliance of the valve was tested by using a heart pulsed flow simulator system. The results (FIG. 12) confirmed that the Nitinol mesh sheet, which dominates the mechanical properties of the leaflet material, has stiffness that is appropriate for valve function. This was achieved by using an extra thin superelastic Nitinol mesh (25 microns thickness) and also by proper attachment of the leaflets to the valve stand. The design of the Nitinol mesh leaflets is in a way to reduce the amount of stress applied to cells inside the blood. The dimensions of holes in the mesh and its thickness were chosen not to have a significant effect on the remodeling of the finally formed tissue. An opening size of about 0.0088", which is almost 10 times larger than the dimension of the circulatory/stationary/migratory cells of the body, minimizes the effect of the metal on the in vivo formed tissue natural remodeling. A higher stiffness mismatch could lead to tissue detachment and immediate clotting or stimulated and excessive tissue growth.

It is understood that the examples and embodiments described herein are for illustrative purposes only and that various modifications or changes in light thereof will be suggested to persons skilled in the art and are to be included within the spirit and purview of this application and scope of any appended claims. All figures, tables, and appendices, as well as publications, patents, and patent applications, cited herein are hereby incorporated by reference in their entirety for all purposes.

What is claimed is:

1. A heart valve comprising a heart valve leaflet comprising a metal mesh material, wherein the metal mesh material comprises openings having dimensions of 0.0005-0.0200 inches, wherein the metal mesh has a thickness of 0.0004-0.0100 inches, wherein the leaflet functionally mimics a heart valve leaflet, and wherein the heart valve is compliant enough to open and close in response to a flow rate as low as 3 L/min.

2. The heart valve of claim 1, wherein the metal has shape memory or is superelastic.

3. The heart valve of claim 1, wherein the leaflet is configured to capture circulatory/stationary/migratory cells, when implanted in a body of a subject, to become biologically active.

4. The heart valve of claim 1, wherein the leaflet has a modified surface, which facilitates growth of a tissue layer on the leaflet, such that the mesh may become enclosed in the tissue layer.

5. The heart valve of claim 4, wherein said modified surface comprises a bioactive material coating on the leaflet, wherein said bioactive material is configured to capture and/or actively recruit cells and/or provide cell differentiation guidance.

6. The heart valve of claim 5, wherein the bioactive material is selected from the group consisting of a molecule that binds to a cell adhesion molecule (CAM), a growth factor, an extracellular matrix molecule, a subendothelial extracellular matrix molecule and a peptide.

7. The heart valve of claim 6, wherein the molecule that binds to a CAM is a CD34 antibody.

8. The heart valve of claim 6, wherein the growth factor is selected from the group consisting of epidermal growth factor (EGF), fibroblast growth factor 1 (FGF1), FGF2, FGF3, FGF4, vascular endothelial growth factor-A (VEGF-A), VEGF-B, VEGF-C, VEGF-D, and placental growth factor (PGF).

9. The heart valve of claim 6, wherein the subendothelial extracellular matrix molecule is selected from the group consisting of fibulin-5 and fibrillin-1.

10. The heart valve of claim 6, wherein the peptide is an RGD-peptide.

11. The heart valve of claim 4, wherein the surface of the leaflet is modified by plasma coating.

12. The heart valve of claim 4, wherein the surface of the mesh is micropatterned to enhance cell binding.

13. The heart valve of claim 1, wherein the mesh has opening dimensions of about 0.0088 inches.

14. The heart valve of claim 1, wherein the mesh has a thickness of about 0.001 inches.

15. The heart valve of claim 1, wherein the metal is nitinol or stainless steel.

16. The heart valve of claim 1, further comprising at least one layer of cells at each side of the metal mesh material, wherein the at least one layer of cells encloses the metal mesh material, such that the at least one layer of cells on the first side interacts with the at least one layer of cells on the second side through the network of holes to provide structure integration.

17. The heart valve of claim 1, further comprising at least two layers of cells at each side of the metal mesh material, wherein the at least two layers of cells enclose the metal mesh material, such that the at least two layers of cells on the first side interacts with the at least two layers of cells on the second side through the network of holes to provide structure integration.

18. The heart valve of claim 1, further comprising at least three layers of cells at each side of the metal mesh material, wherein the at least three layers of cells enclose the metal mesh material, such that the at least three layers of cells on the first side interacts with the at least three layers of cells on the second side through the network of holes to provide structure integration.

* * * * *